(12) United States Patent
Heyward

(10) Patent No.: US 9,884,110 B2
(45) Date of Patent: Feb. 6, 2018

(54) METHODS AND COMPOSITIONS FOR ELICITING AN IMMUNE RESPONSE AGAINST HEPATITIS B VIRUS

(71) Applicant: Dynavax Technologies Corporation, Berkeley, CA (US)

(72) Inventor: William L. Heyward, Oakland, CA (US)

(73) Assignee: Dynavax Technologies Corporation, Berkeley, CA (US)

( * ) Notice: Subject to any disclaimer, the term of this patent is extended or adjusted under 35 U.S.C. 154(b) by 0 days.

(21) Appl. No.: 15/264,498

(22) Filed: Sep. 13, 2016

(65) Prior Publication Data

US 2017/0087245 A1  Mar. 30, 2017

Related U.S. Application Data

(63) Continuation of application No. 13/448,302, filed on Apr. 16, 2012, now Pat. No. 9,452,212.

(60) Provisional application No. 61/559,054, filed on Nov. 12, 2011, provisional application No. 61/475,548, filed on Apr. 14, 2011.

(51) Int. Cl.
*A61K 39/29* (2006.01)
*A61K 39/39* (2006.01)
*C12N 7/00* (2006.01)
*A61K 39/00* (2006.01)

(52) U.S. Cl.
CPC ............ *A61K 39/292* (2013.01); *A61K 39/39* (2013.01); *C12N 7/00* (2013.01); *A61K 2039/545* (2013.01); *A61K 2039/55561* (2013.01); *A61K 2039/575* (2013.01); *C12N 2730/10134* (2013.01); *C12N 2730/10171* (2013.01)

(58) Field of Classification Search
CPC ........ A61K 2039/5254; A61K 2039/53; A61K 2039/57; A61K 31/713; A61K 2039/525; A61K 2039/5256; A61K 2039/55511; C12N 7/00; C12N 15/113; C12N 2770/20033
See application file for complete search history.

(56) References Cited

U.S. PATENT DOCUMENTS

| | | | |
|---|---|---|---|
| 4,710,463 A | 12/1987 | Murray | |
| 4,769,238 A | 9/1988 | Rutter et al. | |
| 5,453,496 A | 9/1995 | Caruthers et al. | |
| 5,741,674 A | 4/1998 | Schweden et al. | |
| 5,972,346 A | 10/1999 | Hauser et al. | |
| 6,207,646 B1 | 3/2001 | Krieg et al. | |
| 6,268,122 B1 | 7/2001 | Murray | |
| 6,270,955 B1 | 8/2001 | Murray | |
| 6,287,586 B1 | 9/2001 | Orvig et al. | |
| 6,297,355 B1 | 10/2001 | Murray | |
| 6,475,489 B1 | 11/2002 | Rutter et al. | |
| 6,544,757 B1 | 4/2003 | Rutter et al. | |
| 6,589,940 B1 | 7/2003 | Raz et al. | |
| 7,727,712 B2 | 6/2010 | Van Nest et al. | |
| 8,372,413 B2 | 2/2013 | Fearon et al. | |
| 9,452,212 B2 | 9/2016 | Heyward | |
| 2008/0066741 A1 | 3/2008 | LeMahieu | |
| 2008/0207550 A1 | 8/2008 | Fearon et al. | |
| 2011/0229524 A1 | 9/2011 | Fritsche et al. | |

FOREIGN PATENT DOCUMENTS

WO  WO-2009/055076 A2  4/2009
WO  WO-2012/138325 A1  10/2012

OTHER PUBLICATIONS

DaRoza G, Loewen A, Djurdjev O, Love J, Kempston C, Burnett S, Kiaii M, Taylor PA, Levin A. Stage of chronic kidney disease predicts seroconversion after hepatitis B immunization: earlier is better. Am J Kidney Dis. Dec. 2003;42(6):1184-92.*
Alavian et al. (May 14, 2010, e-pub. Apr. 4, 2010). "The Effect of Diabetes Mellitus on Immunological Response to Hepatitis B Virus Vaccine in Individuals with Chronic Kidney Disease: A Meta-Analysis of Current Literature," *Vaccine* 28(22):3773-3777.
American Diabetes Association. (2013). "Fast facts: data and statistics about diabetes." Located at http://professional.diabetes.org/admin/UserFiles/0%20-%20Sean/14_fast_facts_june2014_final3.pdf, Last visted on Sep. 2, 2014, 2 pages.
American Diabetes Association. (2010). "Diagnosis and classification of diabetes mellitus." *Diabetes Care.* 33(Suppl 1):S62-S69.
Andre et al. (1987). "Summary of Clinical Findings on Engerix-B, A Genetically Engineered Yeast-Derived Hepatitis B Vaccine," *Postgrad. Med. J.* 63(Suppl. 2):169-177.
Averhoff et al. (1998). "Immunogenicity of Hepatitis B Vaccines. Implications for Persons at Occupational Risk of Hepatitis B Virus Infection," *Am. J. Prev. Med.* 15(1):1-8.
Barry et al. (2007). "Review of Hepatitis B Surface Antigen-1018 ISS Adjuvant-Containing Vaccine Safety and Efficacy," *Expert Opinion Biol. Ther.* 7(11):1731-1737.
Beran (2008). "Safety and Immunogenicity of a New Hepatitis B Vaccine for the Protection of Patients with Renal Insufficiency Including Pre-Haemodialysis and Haemodialysis Patients," *Expert Opin. Biol. Ther.* 8(2):235-247.
Bessman et al. (1992). "Infections in the Diabetic Patient: The Role of Immune Dysfunction and Pathogen Virulence Factors," *J. Diabetes Complications* 6:258-262.

(Continued)

*Primary Examiner* — Rachel B Gill

(74) *Attorney, Agent, or Firm* — Morrison and Foerster LLP

(57) ABSTRACT

The present invention relates to immunization of hyporesponsive groups of individuals. In particular, the present invention provides methods and compositions for eliciting a potent immune response to hepatitis B virus in individuals in need thereof.

14 Claims, 4 Drawing Sheets

(56) References Cited

OTHER PUBLICATIONS

Bird (1986). "CpG-Rich Islands and the Function of DNA Methylation," *Nature* 321(6067):209-213.
Bouter et al. (1992). "Humoral Immune Response to a Yeast-Derived Hepatitis B Vaccine in Patients with Type 1 Diabetes Mellitus," *Diabet. Med.* 9:66-69.
Braun et al. (1988). "Immunogenic Duplex Nucleic Acids Are Nuclease Resistant," *J. Immunol.* 141(6):2084-2089.
Casqueiro et al. (2012). "Infections in Patients with Diabetes Mellitus: A Review of Pathogenesis," *Indian J. Endocrinol Metab.* 16:S27-S36.
Centers for Disease Control and Prevention (CDC). (2011). "Use of Hepatitis B Vaccination for Adults with Diabetes Mellitus: Recommendations of the Advisory Committee on Immunization Practices (ACIP)," *MMWR.* 60:1709-1711.
Centers for Disease Control and Prevention (CCD). (2012). "Recommended Adult Immunization Schedule—United States, 2012," *MMWR.* 61:1-7.
Chaturvedi et al. (1996). "Stabilization of Triple-Stranded Oligonucleotide Complexes: Use of Probes Containing Alternating Phosphodiester and Stereo-Uniform Cationic Phosphoramidate Linkages," *Nucleic Acids Res.* 24(12):2318-2323.
Chin (2003). "Hepatitis B Virus Vaccine Response in Hemodialysis: Baseline Patient Characteristics," *Hemodial Int.* 7:296-303.
Cho et al. (2000). "Immunostimulatory DNA-Based Vaccines Induce Cytotoxic Lymphocyte Activity by a T-Helper Cell-Independent Mechanism," *Nature Biotechnology* 18(5):509-514.
ClinicalTrials.gov Identifier NCT00426712. (first received Jan. 23, 2007, last updated Jul. 20, 2010). "Safety of HEPLISAV™ Hepatitis B Virus Vaccine in End-Stage Kidney Failure Patients," DV2-HBV-09, located at http://clinicaltrials.gov/ct2/show/NCT00426712?term=dynavax&rank=2, last visited on Nov. 3, 2011, 4 pages.
ClinicalTrials.gov Identifier NCT00435812. (first received Feb. 13, 2007, last updated Jan. 18, 2008). "Safety and Efficacy of HEPLISAV™ Hepatitis B Virus Vaccine Compared with Engerix-B® Vaccine," DV2-HBV-10, located at http://clinicaltrials.gov/ct2/show/NCT00435812?term=dynavax&rank=4, last visited on Nov. 3, 2011, 4 pages.
ClinicalTrials.gov Identifier NCT00498212. (first received Jul. 5, 2007, last updated Oct. 6, 2008). "A Safety and Efficacy Study of a Single or Double Dose of HEPLISAV™ Hepatitis B Vaccine in Adults with End-Stage Renal Disease," DV2-HBV-11, located at http://clinicaltrials.gov/ct2/show/NCT00498212?term=dynavax&rank=5, last visited on Nov. 3, 2011, 4 pages.
ClinicalTrials.gov Identifier NCT00511095. (first received Jul. 25, 2007, last updated Jun. 17, 2010). "Open-Label Study of the Safety and Immunogenicity of HEPLISAV™ Hepatitis B Virus Vaccine," DV2-HBV-14, located at http://clinicaltrials.gov/ct2/show/NCT00511095?term=dynavax&rank=9, last visited on Nov. 3, 2011, 4 pages.
ClinicalTrials.gov Identifier NCT01005407. (first received Oct. 29, 2009, last updated Jun. 17, 2010). "Safety, Immunogenicity, Lot-to-Lot Consistency Study of the HBV Vaccine, HEPLISAV™ Compared to Engerix-B® Vaccine," DV2-HBV-16, located at http://clinicaltrials.gov/ct2/show/NCT01005407?term=dynavax&rank=11, last visited on Nov. 3, 2011, 3 pages.
ClinicalTrials.gov Identifier NCT00985426. (first received Sep. 24, 2009, last updated Feb. 15, 2011). "Immunogenicity and Safety of HEPLISAV™ Hepatitis B Virus Vaccine in Chronic Kidney Disease (CKD) Patients," DV2-HBV-17, located at http://clinicaltrials.gov/ct2/show/NCT00985426?term=dynavax&rank=12, last visited on Nov. 3, 2011, 4 pages.
ClinicalTrials.gov Identifier NCT01195246. (first received Sep. 2, 2010, last updated Jan. 11, 2011). "Safety and Immunogenicity of HEPLISAV™ a Hepatitis B Virus Vaccine in Adults on Hemodialysis," DV2-HBV-18, located at http://clinicaltrials.gov/ct2/show/NCT01195246?term=dynavax&rank=14, last visited on Nov. 3, 2011, 4 pages.
ClinicalTrials.gov Identifier NCT01282762. (first received Jan. 20, 2011, last updated Jan. 21 2011). "Long-Term Study on Safety and Immunogenicity of HEPLISAV™ and Engerix-B® in Adults with Chronic Kidney Disease," DV2-HBV-19, located at http://clinicaltrials.gov/ct2/show/NCT01282762?term=dynavax&rank=16, last visited on Nov. 3, 2011, 4 pages.
Cooper et al. (2008). "CPG 7909 Adjuvant Plus Hepatitis B Virus Vaccination in HIV-Infected Adults Achieves Long-Term Seroprotection for Up to 5 years," *CID* 46(8):1310-1314.
Cooper et al. (2011). "Hepatitis B Surface Antigen-1018 ISS Adjuvant-Containing Vaccine a Review of HEPLISAV™ Safety and Efficacy," *Expert Rev. Vaccines* 10(4):417-427.
Cowdery et al. (1996). "Bacterial DNA Induces NK Cells to Produce IFN-γ In Vivo and Increases the Toxicity of Lipopolysaccharides," *J. Immunol.* 156(12):4570-4575.
Demir et al. (2008). "The Prevalence of Occult Hepatitis B Virus Infection in Type 2 Diabetes Mellitus Patients," *Eur. J. Gastroenterol Hepatol.* 20(7):668-673.
Denis et al. (1984). "Hepatitis-B Vaccination in the Elderly," *J. Inf. Dis.* 149(6):1019.
Domingo et al. (2012). "Response to Vaccination Against Hepatitis B Virus with a Schedule of Four 40-µg Doses in Cirrhotic Patients Evaluated for Liver Transplantation: Factor Associated with a Response," *Transplant Proc.* 44:1499-1501.
Dorrell et al. (1997). "Clinical and Serological Responses to an Inactivated Influenza Vaccine in Adults with HIV Infection, Diabetes, Obstructive Airways Disease, Elderly Adults and Healthy Volunteers," *International Journal of STD & AIDS* 8(12):776-779.
Douvin et al. (1997). "Hepatitis B Vaccination in Diabetic Patients. Randomized Trial Comparing Recombinant Vaccines Containing and Not Containing Pre-S2 Antigen," *Diabetes Care* 20(2):148-151.
ENGERIX-B [Hepatitis B Vaccine (Recombinant)]. (Dec. 2010, Revised Oct. 2011). Package Insert. GlaxoSmithKline Biologicals, Research Triangle Park, NC, 13 pages.
Fendrix emc Medicine Guides. (2010, last updated Jan. 31, 2012). Provided by www.medicines.org.uk/guides, 2 pages.
Friedberg et. al. (2005). "Combination immunotherapy with a CpG oligonucleotide (1018 ISS) and rituximab in patients with non-Hodgkin lymphoma: increased interferon-alpha/beta-inducible gene expression, without significant toxicity," *Blood* 105(2):489-95.
Geerlings et al. (1999). "Immune Dysfunction in Patients with Diabetes Mellitus (DM)," *FEMS Immunology and Medical Microbiology* 26(3-4):259-265.
Halpern et al. (1996). "Bacterial DNA Induces Murine Interferon-γ Production by Stimulation of Interleukin-12 and Tumor Necrosis Factor-α," *Cell Immunology* 167(1):72-78.
Halperin et al. (2003). "A Phase I Study of the Safety and Immunogenicity of Recombinant Hepatitis B Surface Antigen Co-Administered with an Immunostimulatory Phosphorothioate Oligonucleotide Adjuvant," *Vaccine* 21(19-20):2461-2467.
Halperin et al. (2006). "Comparison of the Safety and Immunogenicity of Hepatitis B Virus Surface Antigen Co-Administered with an Immunostimulatory Phosphorothioate Oligonucleotide and a Licensed Hepatitis B Vaccine in Healthy Young Adults," *Vaccine* 24(1):20-26.
Halperin et al. (2009). "Preliminary results from 2 studies comparing immunogenicity of two doses of HBsAg combined with immunostimulatory sequence (ISS) in chronic renal failure (CRF) patients." 47th Ann. Meeting of the Infectious Disease Society of America. Philadelphia, PA. 1 Page.
Halperin et al. (2012, e-pub. Feb. 9, 2012). "Comparison of Safety and Immunogenicity of Two Doses of Investigational Hepatitis B Virus Surface Antigen Co-Administered with an Immunostimulatory Phosphorothioate Oligodeoxyribonucleotide and Three Doses of a Licensed Hepatitis B Vaccine in Healthy Adults 18-55 Years of Age," *Vaccine* 30:2556-2563.
Halperin et al. (2012, e-pub. Jun. 13, 2012). "Safety and Immunogenicity of Different Two-Dose Regimens of an Investigational Hepatitis B Vaccine (Hepatitis B Surface Antigen Co-Administered with an Immunostimulatory Phosphorothioate Oligodeoxyribonucleotide) in Healthy Young Adults," *Vaccine* 30:5445-5448.

(56) References Cited

OTHER PUBLICATIONS

Halperin et al. (2013). "Immunogenicity of an Investigational Hepatitis B Vaccine (Hepatitis B Surface Antigen Co-Administered with an Immunostimulatory Phosphorothioate Oligodeoxyribonucleotide) in Nonresponders to Licensed Hepatitis B Vaccine," *Human Vaccines & Immunotherapeutics* 9:1438-1444.
Harris (2005). "Elevated liver function tests in type 2 diabetes," *Clin. Diabetes.* pp. 115-119.
Hartmann et al. (2000). "Mechanism and function of a newly identified CpG DNA motif in human primary B cells." *J Immunol.* 164(2):944-53.
Heyward et al. (Oct. 23, 2010). "Immunogenicity of Two Doses of Investigational HEPLISAV™ (HBsAg-ISS) Compared to Three Doses of Licensed Hepatitis B Vaccine (ENGERIX-B®) in Diabetics." Slide Deck of Oral Presentation made at the *48th Annual Meeting of the Infectious Disease Society of America Meeting*, Vancouver, BC, 15 pages.
Heyward et al. (Oct. 23, 2010). "Immunogenicity of Two Doses of Investigational HEPLISAV™ (HBsAg-ISS) Compared to Three Doses of Licensed Hepatitis B Vaccine (ENGERIX-B®) in Diabetics." Oral Abstract Session, presented at the *48th Annual Meeting of the Infectious Disease Society of America Meeting*, Vancouver, BC, Oct. 21-24, 2010, Abstract No. LB-53, located at http://idsa.confex.com/idsa/2010/webprogram/Paper5115.html, last visited on Mar. 22, 2011, 2 pages.
Heyward et al. (Nov. 1, 2010). "Immunogenicity of Two Doses of Investigational HEPLISAV™ (HBsAg-1018 ISS) Compared to Three Doses of Licensed Hepatitis B Vaccine (ENGERIX-B®) in Diabetics," Poster, presented at the *American Association for the Study of Liver Diseases Meeting*, Boston, MA, Oct. 29-Nov. 2, 2010, 1 page.
Heyward et al. (Oct. 21, 2011). "Immunogenicity of Two Doses of Investigational HEPLISAV™ (HBsAg-1018 ISS) Compared to Three Doses of Licensed Hepatitis B Vaccine (ENGERIX-B®) in Type II Diabetics." Poster, presented at the *49th Annual Meeting of the Infectious Disease Society of America and the HIV Medicine Association Meeting*, Boston, MA, Oct. 20-23, 2011, IDSA Poster No. 721, 1 page.
Heyward et al. (Nov. 6, 2011). "Immunogenicity of Two Doses of Investigational HEPLISAV™ (HBsAg-1018 ISS) Compared to Three Doses of Licensed Hepatitis B Vaccine (ENGERIX-B®) in Hypo-Responsive Populations." Poster, presented at the *62nd Annual Meeting of the American Association for the Study of Liver Diseases Meeting*, San Francisco, CA, Nov. 5-8, 2011, 1 page.
Heyward et al. (2013). "Immunogenicity and Safety of an Investigational Hepatitis B Vaccine with Toll-Like Receptor 9 Agonist Adjuvant (HBsAg-1018) Compared to a Licensed Hepatitis B Vaccine in Healthy Adults 40-70 Years of Age," *Vaccine.* 31:5300-5305.
Jäger et al. (1988). "Oligonucleotide N-Alkylphosphoramidates: Synthesis and Binding to Polynucleotides," *Biochemistry* 27(19):7237-7246.
Janssen et al. (Nov. 12, 2011). "Immunogenicity of Investigational HEPLISAV™ Compared with Licensed Hepatitis B Vaccine (Engerix-B®) in Patients with Chronic Kidney Disease." Poster, presented at the *44th Annual Meeting of the American Society of Nephrology Kidney Week 2011*, Philadelphia, PA, Nov. 8-13, 2011, 1 page.
Janssen et al. (2013). "Immunogenicity and Safety of an Investigational Hepatitis B Vaccine with Toll-Like Receptor 9 Agonist Adjuvant (HBsAg-1018) Compared with a Licensed Hepatitis B Vaccine in Patients with Chronic Kidney Disease," *Vaccine.* 31:5306-5313.
Joshi et al. (1999). "Infections in Patients with Diabetes Mellitus," *N. Engl. J. Med.* 341:1906-1912.
Karakus et al. (2007). "Determinants of Protection Against Diphtheria in Adult Hemodialysis Patients," *Ren. Fail.* 29:829-834.
Keating et al. (2003). "Recombinant Hepatitis B Vaccine (Engerix-B): A Review of Its Immunogenicity and Protective Efficacy Against Hepatitis B," *Drugs* 63(10):1021-1051.
Kilic et al. (2003). "Seroprevalence of Tetanus Immunity Among Noninsulin-Dependent Diabetes Mellitus Patients," *J. Diabetes Complications* 17:258-263.
Klinman et al. (1996). "CpG Motifs Present in Bacteria DNA Rapidly Induce Lymphocytes to Secrete Interleukin 6, Interleukin 12, and Interferon γ," *PNAS USA* 93(7):2879-2883.
Krieg et al. (1995). "CpG Motifs in Bacterial DNA Trigger Direct B-Cell Activation," *Nature* 374:546-549.
Kuan et al. (2013). "Cost-Effectiveness of Hepatitis B Vaccination Using HEPLISAV™ in Selected Adult Populations Compared to Engerix-B® Vaccine," *Vaccine.* 31:4024-4032.
Latimer et al. (1995). "Specificity of Monoclonal Antibodies Produced Against Phosphorothioate and Ribo Modified DNAs," *Molecular Immunology* 32(14/15):1057-1064.
Madaan (2009). "HEPLISAV™. Hepatitis B Vaccine," *Drugs of the Future* 34(7):531-535.
Magnius et al. (1995). "Subtypes, Genotypes and Molecular Epidemiology of the Hepatitis B Virus as Reflected by Sequence Variability of the S-Gene," *Intervirology* 38(1-2):24-34.
McNeil et al. (Oct. 31, 2009). "Preliminary Results from Two Studies Comparing Immunogenicity of Three Doses of HBsAg Combined with Immunostimulatory Sequence (ISS) in Chronic Renal Failure (CRF) Patients," Poster, presented at the *47th Annual Meeting of the Infectious Disease Society of America Meeting*, Philadelphia, MA, 1 page.
McNeil et al. (Apr. 14, 2010). "Safety and Immunogenicity of a Novel Hepatitis B Vaccine Adjuvanted with Immunostimulatory Sequence (ISS) in Renal Predialysis and Dialysis Patients," Abstract of Poster, presented at the *National Kidney Foundation Spring Clinical Meeting*, Orlando, FL, 1 page.
McNeil et al. (Apr. 14, 2010). "Safety and Immunogenicity of a Novel Hepatitis B Vaccine Adjuvanted with Immunostimulatory Sequence (ISS) in Renal Predialysis and Dialysis Patients," Poster, presented at the *National Kidney Foundation Spring Clinical Meeting*, Orlando, FL, 1 page.
Menzin et al. (2010). "Relationship Between Glycemic Control and Diabetes-Related Hospotal Costs in Patients with Type 1 or Type 2 Diabetes Mellitus," *J. Manag. Care Pharm.* 16:264-275.
Messina et al. (1991). "Stimulation of In Vitro Murine Lymphocyte Proliferation by Bacterial DNA," *J. Immunol.* 147(6):1759-1764.
Miller et al. (1971). "Syntheses and Properties of Adenine and Thymine Nucleoside Alkyl Phosphotriesters, the Neutral Analogs of Dinucleoside Monophosphates," *J Am Chem Soc.* 93(24):6657-6665.
Moutschen et al. (1992). "Impaired Immune Responses in Diabetes Mellitus: Analysis of the Factors and Mechanisms Involved. Relevant to the Increased Susceptibility of Diabetic Patients to Specific Infections," *Diabet. & Metabolism* 18:187-201.
National Foundation for Infectious Diseases. (2009). Biography of "Stanley A. Plotkin, MD: Recipient of the 2009 Maxwell Finland Award for Scientific Achievement," located at http://www.nfid.org/awards/plotkin.pdf, last visited on Jul. 16, 2014, 3 pages.
Nelson et al. (1997). "N3'→P5' Oligodeoxyribonucleotide Phosphoramidates: A New Method of Synthesis Based on a Phosphoramidite Amine-Exchange Reaction," *J. Org. Chem.* 62(21):7278-7287.
Nelson et al. (2009). "Compliance with Multiple-Dose Vaccine Schedules," *Am. J. Public Health* 99:S389-S397.
Park et al. (2010). "The Production and Immunostimulatory Activity of Double-Stranded CpG-DNA," *Korean Society Biochem. Mol. Biol.* 43(3):164-169.
Payette et al. (2006). "Testing of CpG-Optimized Protein and DNA Vaccines Against the Hepatitis B Virus in Chimpanzees for Immunogenicity and Protection from Challenge," *Intervirology* 49(3):144-151.
Peleg et al. (2007). "Common Infections in Diabetes: Pathogenesis, Management and Relationship to Glycaemic Control," *Diabetes Metab. Res. Rev.* 23:3-13.
Peyrottes et al. (1996). "Oligodeoxynucleoside Phosphoramidates (P-NH₂): Synthesis and Thermal Stability of Duplexes with DNA and RNA Targets," *Nucleic Acids Research* 24(10):1841-1848.
Pisetsky (1996). "Immune Activation by Bacterial DNA: A New Genetic Code," *Immunity* 5(4):303-310.

(56) References Cited

OTHER PUBLICATIONS

Pozzilli et al. (1987). "Reduced Protection Against Hepatitis B Virus Following Vaccination in Patients with Type 1 (Insulin-Dependent) Diabetes," *Diabetologia* 30(10):817-819.
Pozzilli et al. (1994). "Infections and Diabetes: Mechanisms and Prospects for Prevention," *Diabet. Med.* 11:935-941.
Pyles et al. (2002). "Use of immunostimulatory sequence containing oligonucleotides as topical therapy for genital herpes simplex virus type 2 infection." J Virol. 76(22):11387-96.
Recombinax HB® [Hepatitis B Vaccine (Recombinant)]. (Dec. 2010). Package Insert. Merck & Co., Inc., Whitehouse Station, NJ, 13 pages.
Roman et al. (1997). "Immunostimulatory DNA Sequences Function As T Helper-1-Promoting Adjuvants," *Nature Medicine* 3(8):849-854.
Sablan et al. (2012). "Demonstration of Safety and Enhanced Seroprotection Against Hepatitis B with Investigational HBsAg-1018 ISS Vaccine Compared to a Licensed Hepatitis B Vaccine," *Vaccine* 30:2689-2696.
Sampanis. (2008). "Management of hyperglycemia in patients with diabetes mellitus and chronic renal failure," *Hippokratia.* 12(1):22-7.
Sato et al. (1996). "Immunostimulatory DNA Sequences Necessary for Effective Intradermal Gene Immunization," *Science* 273:352-354.
Schaffner et. al. "Hepatitis B: Why Should I Care?" 2010 Investor and Anaylst Day Slide Deck. Dynavax Analyst & Investor Breakfast. Oct. 29, 2010, 8:00 AM EST. New York, NY. 77 pages. http://files.shareholder.com/downloads/DVAX/0x0x413901/74707c45-c40f-4073-9c82-e697b5aa66ea/MASTER_fri_morning_MASTER_all_slides_DVAX_Investor_Day.pdf.
Schillie et al. (2012). "Immune Response of Hepatitis B Vaccine Among Persons with Diabetes," *Diabetes Care* 35:2690-2697.
Schultz et al. (1996). "Oligo-2'-Fluoro-2'-Deoxynucleotide N3'→P5' Phosphoramidates: Synthesis and Properties," *Nucleic Acids Research* 24(15):2966-2973.
Stirchak et al. (1989). "Uncharged Stereoregular Nucleic Acid Analogs: 2. Morpholino Nucleoside Oligomers with Carbamate Internucleoside Linkages," *Nucleic Acids Research* 17(15):6129-6141.
Sung et al. (2006). "HBV-ISS Dynavax," *Current Opinion in Molecular Therapeutics* 8(2):150-155.
Takahashi et al. (1990). "Induction of CD8$^+$ Cytotoxic T Cells by Immunization with Purified HIV-1 Envelope Protein in ISCOMs," *Nature* 344(6269):873-875.
Tighe et al. (2000). "Conjugation of Protein to Immunostimulatory DNA Results in a Rapid, Long-Lasting and Potent Induction of Cell-Mediated and Humoral Immunity," *Eur. J. Immunol.* 30(7):1939-1947.
Tiollais et al. (1985). "The Hepatitis B Virus," *Nature* 317(6037):489-495.
Tohme et al. (2011). "Evaluation of Hepatitis B Vaccine Immunogenicity Among Older Adults During an Outbreak Response in Assisted Living Facilities," *Vaccine* 29(50):9316-9320.
Tokunaga et al. (1992). "Synthetic Oligonucleotides with Particular Base Sequences from the cDNA Encoding Proteins of *Mycobacterium bovis* BCG Induce Interferons and Activate Natural Killer Cells," *Microbiol. Immunol.* 36(1):55-66.
Tong et al. (2005). "Immunogenicity and Safety of an Adjuvanted Hepatitis B Vaccine in Pre-Hemodialysis and Hemodialysis Patients," *Kidney International* 68:2298-2303.
Treadwell et al. (1993). "Immunogenicity of Two Recombinant Hepatitis B Vaccines in Older Individuals," *Am. J. Med.* 95(6):584-588.
Valenzuela et al. (1982). "Synthesis and Assembly of Hepatitis B Virus Surface Antigen Particles in Yeast," *Nature* 298(5872):347-350.
Vandepapeliere et al. (2008). "Vaccine Adjuvant Systems Containing Monophosphoryl Lipid A and QS21 Induce Strong and Persistent Humoral and T Cell Responses Against Hepatitis B Surface Antigen in Healthy Adult Volunteers," *Vaccine* 26:1375-1386.
Vollmer et al. (2009). "Immunotherapeutic applications of CpG oligodeoxynucleotide TLR9 agonists," *Adv Drug Deliv Rev.* 61(3):195-204.
The Wayback Machine. www.web.archive.org. Accessed Sep. 29, 2015 regarding http://investors.dynavax.com/newsevents.cfm?Year=&ReleasesType=&PageNum=3 and other associated Dynavax pages.
Weber et al. (1985). "Obesity as a Predictor of Poor Antibody Response to Hepatitis B Plasma Vaccine," *Jama* 254(22):3187-3189.
Wismans et al. (1991). "A Prospective Study of In Vitro Anti-HBs Producing B Cells (Spot-ELISA) Following Primary and Supplementary Vaccination with a Recombinant Hepatitis B Vaccine in Insulin Dependent Diabetic Patients and Matched Controls," *J. Med. Virol.* 35(3):216-222.
Yamamoto (1988). "In vitro Augmentation of Natural Killer Cell Activity and Production of Interferon-α/β and -γ with Deoxyribonucleic Acid Fraction From *Mycobacterium bovis* BCG," *Jpn. J. Cancer Res. (Gann)* 79(7):866-873.
Yamamoto et al. (1992). "Unique Palindromic Sequences in Synthetic Oligonucleotides are Required to Induce IFN [Correction of INF] and Augment IFN-Mediated [Correction of INF] Natural Killer Activity," *J. Immunol.* 148(12):4072-4076.
Yap et al. (1995). "Study on the Comparative Immunogenicity of a Recombinant DNA Hepatitis B Vaccine Containing pre-S Components of the HBV Coat Protein with Non pre-S Containing Vaccines," *J. Gastroenterol. Hepatol.* 10(1):51-55, Abstract Only.
International Search Report dated Jul. 27, 2011, for PCT Patent Application No. PCT/US11/31139, filed on Apr. 4, 2011, 3 pages.
Written Opinion dated Jul. 27, 2011, for PCT Patent Application No. PCT/US11/31139, filed on Apr. 4, 2011, 7 pages.
Dynavax Technologies Press Release (Sep. 4, 2002). "Dynavax Initiates Phase II Clincal Trial of ISS Vaccine for Hepatits B—Study Focuses on Single-Injection Approach," 1 page.
Dynavax Technologies Press Release (Jun. 22, 2004). "Dynavax Announces Initiation of Phase II/III Hepatitis B Trial," PRNewswire—FirstCall. 1 page.
Dynavax Technologies Press Release (Sep. 2, 2004). "Dynavax Announces Completion of Enrollment of Phase II/III Hepatitis B Prophylactic Vaccine Trial," PRNewswire—FirstCall. 2 pages.
Dynavax Technologies Press Release (Oct. 20, 2004). "Dynavax to Present Data on Phase 2 Clinical Trial of Hepatitis B Vaccine at ICAAC," PRNewswire—FirstCall. 1 page.
Dynavax Technologies Press Release (Nov. 1, 2004). "Dynavax's Hepatitis B Vaccine Shows More Rapid Immunogenicity, More Durable Protective Response Than Engerix-B in Phase 2 Clinical Trial," PRNewswire—FirstCall. 3 pages.
Dynavax Technologies Press Release (Dec. 9, 2004). "Dynavax Announces Positive Interim Results From Phase 2/3 Hepatitis B Vaccine Trial," PRNewswire—FirstCall. 3 pages.
Dynavax Technologies Press Release (Jun. 14, 2005). "Dynavax Announces Positive Primary Endpoint Results From Phase 2/3 Hepatitis B Vaccine Trial," PRNewswire—FirstCall. 2 pages.
Dynavax Technologies Press Release (Jun. 23, 2005). "Dynavax Initiates Pivotal Phase 3 Trial for Hepatitis B Vaccine," PRNewswire—FirstCall. 2 pages.
Dynavax Technologies Press Release (Sep. 27, 2005). "Dynavax Introduces TOLAMBA™ and HEPLISAV™ Brand Names for Ragweed Allergy and Hepatitis B Vaccine Products," PRNewswire—FirstCall. 2 pages.
Dynavax Technologies Press Release (Nov. 1, 2005). "Dynavax Initiates US-Based Phase 1 Clinical Trial of HEPLISAV-198 Hepatitis B Vaccine in Dialysis Population," PRNewswire—FirstCall. 2 pages.
Dynavax Technologies Press Release (Dec. 7, 2005). "Dynavax to Present Data on Phase 2/3 Clinical Trial of HEPLISAV™ Hepatitis B Vaccine at ICAAC 2005," PRNewswire—FirstCall. 1 page.
Dynavax Technologies Press Release (Dec. 19, 2005). "Dynavax's HEPLISAV™ Hepatitis B Vaccine Shows Statistically Significant Efficacy in Phase 2/3 Clinical Trial," PRNewswire—FirstCall. 3 pages.

(56) References Cited

OTHER PUBLICATIONS

Dynavax Technologies Press Release (Nov. 28, 2006). "Dynavax's HEPLISAV™ Hepatitis B Vaccine Shows Statistically Significant Results in Phase 3 Trial," PRNewswire—FirstCall. 2 pages.

Dynavax Technologies Press Release (Dec. 4, 2006). "Dynavax's HEPLISAV™ Hepatitis B Vaccine Shows 100% Seroprotection Regardless of Vaccination Schedule in Phase 2 Trial," PRNewswire—FirstCall. 2 pages.

Dynavax Technologies Press Release (Dec. 20, 2006). "Dynavax Initiates Pivotal Phase 3 Trial for HEPLISAV™, Hepatitis B Vaccine," PRNewswire—FirstCall. 2 pages.

Dynavax Technologies Press Release (Jun. 26, 2007). "Dynavax Starts HEPLISAV™ Phase 3 in Europe; U.S. Study; and Phase 2 in ESRD in Canada," PRNewswire—FirstCall. 2 pages.

Dynavax Technologies Press Release (Jun. 28, 2007). "Coley Pharmaceutical Group Grants Dynavax License for Commercialization of HEPLISAV™," PRNewswire—FirstCall. 2 pages.

Dynavax Technologies Press Release (Sep. 19, 2007). "Dynavax's HEPLISAV™ Hepatitis B Vaccine Maintains Full Immunogenicity at 50 Weeks in Phase 3 Trial," PRNewswire—FirstCall. 2 pages.

Dynavax Technologies Press Release (Nov. 1, 2007). "Dynavax and Merck & Co., Inc. Announce Partnership to Develop HEPLISAV™, an Investigational Hepatitis B Vaccine Currently in Phase 3," PRNewswire—FirstCall. 2 pages.

Dynavax Technologies Press Release (Mar. 17, 2008). "Dynavax and Merck & Co., Inc. Report Clinical Hold of Investigational Vaccine HEPLISAV," Business Wire. 2 pages.

Dynavax Technologies Press Release (Apr. 17, 2008). "Dynavax and Merck & Co., Inc. Update Status of Clinical Hold of Investigational Vaccine HEPLISAV™," Business Wire. 2 pages.

Dynavax Technologies Press Release (Aug. 5, 2008). "Dynavax and Merck & Co., Inc. Announce Phase 3 Trial with Investigational Hepatitis B Vaccine (HEPLISAV™) Met its Primary Endpoint," Business Wire. 2 pages.

Dynavax Technologies Press Release (Oct. 21, 2008). "Dynavax and Merck & Co., Inc. Provide Update on U.S. FDA Clinical Hold on Investigational Vaccine HEPLISAV™," Business Wire. 2 pages.

Dynavax Technologies Press Release (Dec. 19, 2008). "Dynavax Announces Termination of Partnership with Merck for HEPLISAV™ Hepatitis B Vaccine—All Rights Revert to Dynavax," Business Wire. 2 pages.

Dynavax Technologies Press Release (Feb. 9, 2009). "Dynavax Announces Receipt of Communication from the U.S. FDA on HEPLISAV™ Hepatitis B Vaccine," Business Wire. 1 page.

Dynavax Technologies Press Release (Apr. 27, 2009). "Dynavax Presents Additional Phase 3 Data for HEPLISAV™ Hepatitis B Vaccine at EASL Medical Conference," Business Wire. 2 pages.

Dynavax Technologies Press Release (Jun. 3, 2009). "Dynavax Presents Additional Phase 3 Data for HEPLISAV™ Hepatitis B Vaccine at DDW Medical Conference," Business Wire. 2 pages.

Dynavax Technologies Press Release (Aug. 4, 2009). "Dynavax Announces Path for HEPLISAV™ Hepatitis B Vaccine Development," Business Wire. 2 pages.

Dynavax Technologies Press Release (Aug. 12, 2009). "Dynavax Announces European Development Strategy for HEPLISAV Hepatitis B Vaccine," Business Wire. 2 pages.

Dynavax Technologies Press Release (Sep. 10, 2009). "Dynavax Reports FDA Removes Clinical Hold on HEPLISAV™ Phase 3 Hepatitis B Vaccine," Business Wire. 2 pages.

Dynavax Technologies Press Release (Sep. 22, 2009). "Dynavax Announces HEPLISAV™ Data to Be Presented at IDSA Medical Conference," Business Wire. 1 page.

Dynavax Technologies Press Release (Sep. 29, 2009). "Dynavax Initiates Phase 3 Registration Trial in Chronic Kidney Disease Patients for HEPLISAV™ Hepatitis B Vaccine," Business Wire. 2 pages.

Dynavax Technologies Press Release (Oct. 29, 2009). "Dynavax's HEPLISAV Shows Increased Protection Rate for Chronic Kidney Disease Patients," Business Wire. 2 pages.

Dynavax Technologies Press Release (Dec. 9, 2009). "Dynavax's European Manufacturing Facility Approved for Commercial Production of HEPLISAV Hepatitis B Surface Antigen," Marketwire. 2 pages.

Dynavax Technologies Press Release (Feb. 8, 2010). "Dynavax Initiates Large-Scale Phase 3 Trial of HEPLISAV™," Marketwire. 2 pages.

Dynavax Technologies Press Release (Feb. 16, 2010). "Dynavax Receives Canadian Approval to Conduct Phase 3 Trials of HEPLISAV™," Marketwire. 2 pages.

Dynavax Technologies Press Release (Mar. 16, 2010). "Dynavax Anticipates Earlier BLA Submission for HEPLISAV™," Marketwire. 5 pages.

Dynavax Technologies Press Release (Apr. 14, 2010). "Dynavax's Chronic Kidney Disease Study Confirms HEPLISAV's Enhanced Seroprotection Against HBV Infection," Marketwire. 2 pages.

Dynavax Technologies Press Release (Apr. 27, 2010). "Dynavax's Two Phase 3 HEPLISAV Trials Cleared by DSMB to Continue Immunizations," Marketwire. 2 pages.

Dynavax Technologies Press Release (May 6, 2010). "Dynavax Completes Over 2000 First Immunizations in Phase 3 Study," Marketwire. 2 pages.

Dynavax Technologies Press Release (May 27, 2010). "Dynavax's Two Phase 3 HEPLISAV Trials Cleared by DSMB to Continue Immunizations," Marketwire. 2 pages.

Dynavax Technologies Press Release (Aug. 31, 2010). "NIAID Grant to Fund Dynavax Research on Hepatitis B Vaccination and Individual Variations in Human Responsiveness," Marketwire. 1 page.

Dynavax Technologies Press Release (Sep. 28, 2010). "Dynavax's Two Phase 3 HEPLISAV Trials Cleared by DSMB to Continue," Marketwire. 2 pages.

Dynavax Technologies Press Release (Oct. 4, 2010). "Dynavax's HEPLISAV Demonstrates Superior Seroprotection in Diabetics Compared to Engerix-B," Press Release by Marketwire via Comtex News Network. 2 pages.

Dynavax Technologies Press Release (Oct. 11, 2010). "Dynavax to Report New HEPLISAV™ Data in Diabetics," Press Release by Marketwire via Comtex News Network. 2 pages.

Dynavax Technologies Press Release (Oct. 21, 2010). "Dynavax's HEPLISAV Demonstrates Superior Seroprotection in Diabetics Compared to Engerix-B," Press Release by Marketwire via Comtex News Network. 2 pages.

Dynavax Technologies Press Release (Jan. 10, 2011). "Dynavax Completes Enrollment for Phase 3 Study of HEPLISAV™ in Subjects with Chronic Kidney Disease," Press Release by Market Wire, News Provided by Acquire Media, 2 pages.

Dynavax Technologies Press Release (Feb. 23, 2011) "Dynavax's Two Phase 3 HEPLISAV Trials Cleared by DSMB to Continue to Study Completion," Marketwire. 2 pages.

Dynavax Technologies Press Release (May 25, 2011). "Dynavax Completes Phase 3 Study of HEPLISAV™," Marketwire. 1 page.

Dynavax Technologies Press Release (Jul. 20, 2011). "Dynavax Phase 3 Demonstrates Superiority and Safety of HEPLISAV™ vs. Engerix-B®," Marketwire. 3 pages.

Dynavax Technologies Press Release (Jul. 28, 2011). "FDA Agrees with Dynavax on Consistency of HEPLISAV™ Lots," Marketwire. 2 pages.

Dynavax Technologies Press Release (Sep. 16, 2011). "Dynavax to Report Additional Immunogenicity Data for HEPLISAV™ Phase 3 Trial," Marketwire. 1 page.

Dynavax Technologies Press Release (Sep. 18, 2011). "Dynavax Reports Complete Results from the HEPLISAV™ Phase 3 Trial in Healthy Adults Over Age 40," Marketwire. 2 pages.

Dynavax Technologies Press Release (Oct. 3, 2011). "Dynavax Reports Modified Intent to Treat Analysis from the HEPLISAV™ Phase 3 Trial in Healthy Adults Over Age 40," Marketwire. 2 pages.

Dynavax Technologies Press Release (Oct. 6, 2011). "Dynavax Reports Diabetic Subset Data from Modified Intent to Treat Analysis of the HEPLISAV™ Phase 3 Trial in Healthy Adults Over Age 40," Press Release by Market Wire, News Provided by Acquire Media, 2 pages.

(56) References Cited

OTHER PUBLICATIONS

Dynavax Technologies Press Release (Oct. 10, 2011). "Dynavax Reports Positive Immunogenicity Data from an Analysis of Hypo-Responsive Populations in HEPLISAV™ Phase 3 Trial," Press Release by Market Wire, News Provided by Acquire Media, 2 pages.

Dynavax Technologies Press Release (Oct. 25, 2011). "Data from Two Phase 3 Studies Demonstrate HEPLISAV's Superiority in Immunizing Persons with Diabetes from Hepatitis B," Press Release by Market Wire, News Provided by Acquire Media, 2 pages.

Dynavax Technologies Press Release (Oct. 27, 2011). "Dynavax Phase 3 Data in Chronic Kidney Disease Demonstrates Superiority of HEPLISAV™ vs Engerix-B®," Press Release by Market Wire, News Provided by Acquire Media, 2 pages.

Dynavax Technologies Press Release (Oct. 27, 2011). "Dynavax Confirms HEPLISAV™ Submission Strategies With U.S. FDA and EMA," Marketwire. 2 pages.

Dynavax Technologies Press Release (Feb. 2, 2012). "Dynavax Reports on Heplisav™ Pre-BLA Meeting with FDA," Press Release by Market Wire, News Provided by Acquire Media, 2 pages.

Dynavax Technologies Press Release (Feb. 13, 2012). "Phase 3 Data on HEPLISAV™ in Adults Aged 18-55 Published in VACCINE," Press Release by Market Wire, News Provided by Acquire Media, 2 pages.

Dynavax Technologies Press Release (Mar. 13, 2012). "Phase 3 Data on HEPLISAV™ in Adults Aged 40-70 Published in VACCINE," Press Release by Market Wire, News Provided by Acquire Media, 2 pages.

Dynavax Technologies Press Release (Apr. 26, 2012). "Dynavax Reports HEPLISAV™ BLA Submission," Press Release by Marketwire, News Provided by Acquire Media, 2 pages.

\* cited by examiner

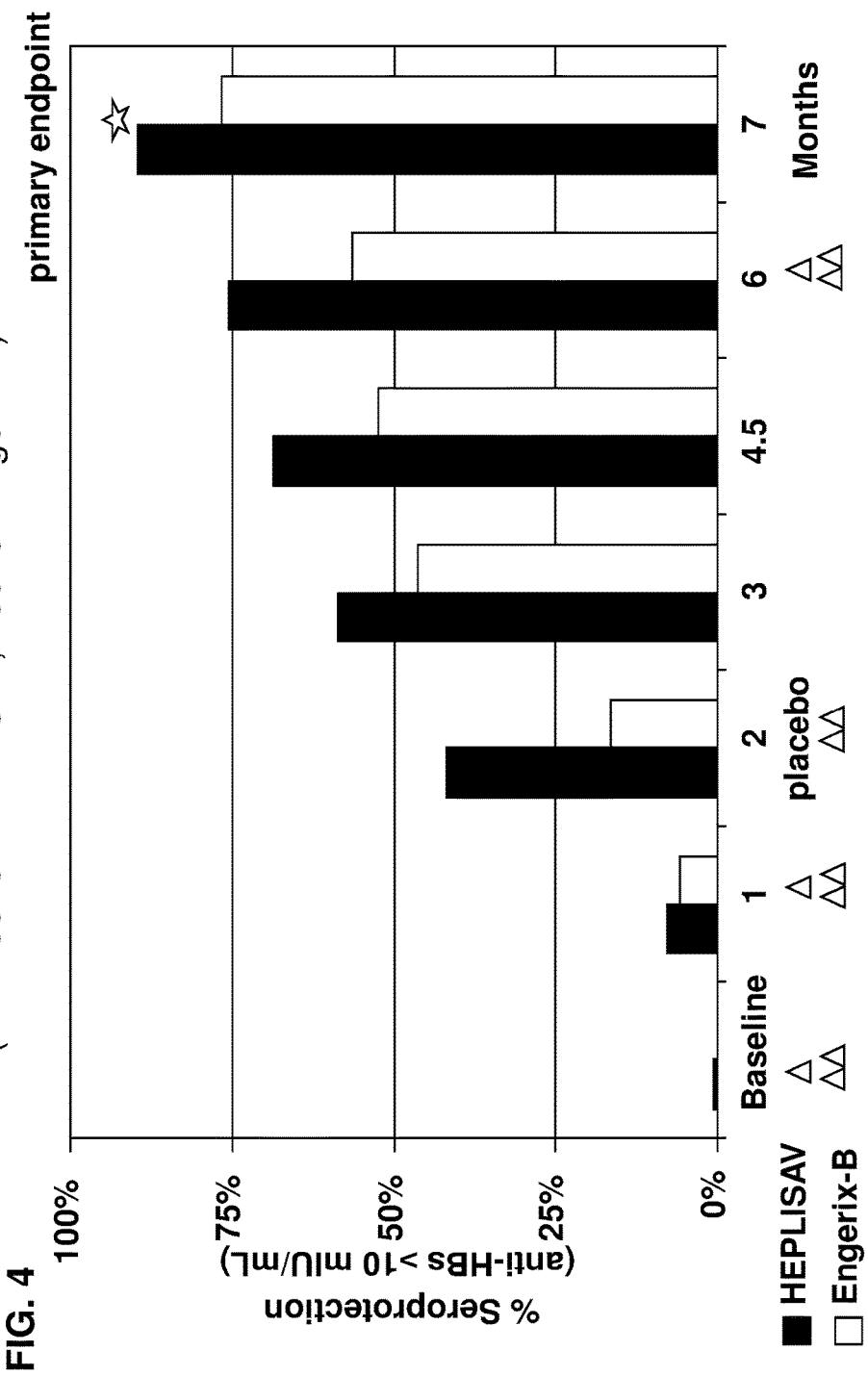

SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: Synthetic Construct

<400> SEQUENCE: 1
tgactgtgaa cgttcgagat ga                                            22

<210> SEQ ID NO 2
<211> LENGTH: 24
<212> TYPE: DNA
<213> ORGANISM: Artificial Sequence
<220> FEATURE:
<223> OTHER INFORMATION: Synthetic Construct

<400> SEQUENCE: 2
tcgtcgtttt gtcgttttgt cgtt                                          24

METHODS AND COMPOSITIONS FOR ELICITING AN IMMUNE RESPONSE AGAINST HEPATITIS B VIRUS

CROSS-REFERENCE TO RELATED APPLICATIONS

This application is a continuation of U.S. application Ser. No. 13/448,302, filed Apr. 16, 2012, now U.S. Pat. No. 9,452,212, which claims the benefit of U.S. Provisional Application No. 61/475,548, filed Apr. 14, 2011, and U.S. Provisional Application No. 61/559,054, filed Nov. 12, 2011, which are hereby incorporated by reference herein in their entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 377882005201SEQLIST.txt, date recorded: Sep. 9, 2016, size: 1 KB).

FIELD

The present invention relates to immunization of hypo-responsive groups of individuals. In particular, the present invention provides methods and compositions for eliciting a potent immune response to hepatitis B virus in individuals in need thereof.

BACKGROUND

Hepatitis B virus (HBV) is one of several viruses known to cause liver disease (e.g., chronic active hepatitis, cirrhosis, liver failure and hepatocellular carcinoma) in humans. HBV is spread through percutaneous or mucosal contact with infected body fluids. According to the World Health Organization (WHO), nearly two billion people are infected with HBV, which causes over 600,000 fatalities each year (WHO, Fact Sheet No. 204, 2009).

The HBV virion is composed of a core antigen (HBcAg), which encapsulates viral DNA, and a surface antigen (HBsAg), which is located on the viral outer membrane. HBsAg, previously known as the Australian antigen, is composed of three glycoproteins having a shared carboxy terminal sequence: S (S only); M (pre-S2 and S); and L (pre-S1, pre-S2 and S). HBsAg self-associates to form 22 nm particles that are released from infected hepatocytes.

All HBV vaccines approved for use in humans are based on noninfectious HBsAg particles. In the United States, the current HBV vaccines are recombinant subunit vaccines produced in yeast (e.g., RECOMBIVAX HB® hepatitis B vaccine marketed by Merck & Co.; and ENGERIX-B® hepatitis B vaccine marketed by GlaxoSmithKline). These HBV vaccines are formulated as HBsAg adsorbed to alum.

Use of the current vaccines is hindered by the typical lengthy administration regimen (e.g., generally three or four doses over six to twelve months). In addition, only 10-20% of adult vaccine recipients mount a seroprotective immune response within one month of receiving a first dose of a HBV vaccine (Andre and Sarary, Post Grad Med J, 63: 169-178, 1987; and Keating and Noble, Drugs 2003, 63:1021-1051, 2003). This delay in the generation of a protective antibody response is of particular importance for individuals at high risk of HBV infection (e.g., health care workers, emergency first responders, or individuals in high-risk behavior groups). Further, compliance in returning for three or four injections over six to twelve months can be poor.

Another serious shortcoming of the current HBV vaccines is the high level of hypo- or non-responders (30-60% hypo- or nonresponders after the recommended regimen) among some groups, such as those over 40 years of age (Denis et al., J Infect Dis, 149:1019, 1984; Averoff et al., Am J Prev Med, 15:1-8, 1998; and Treadwell et al., Am J Med, 95:584-588, 1993), and subjects with renal failure or diabetes (Weber et al., JAMA, 254:3187-3189, 1985). Thus, development of a more potent HBV vaccine with more rapid induction of protective immunity, and improved response among hypo-responder populations is of major importance in reducing HBV infection.

SUMMARY

The present invention relates to immunization of hypo-responsive groups of individuals. In particular, the present invention provides methods and compositions for eliciting a potent immune response to hepatitis B virus in individuals in need thereof.

Specifically, the present disclosure provides methods for eliciting an immune response against hepatitis B virus (HBV) in a human subject having a glucose metabolism disorder, comprising: administering to a human subject a first and a second dose of an immunogenic composition on two separate occasions (e.g., first dose at week 0 and a second dose at week 4), wherein the immunogenic composition comprises a hepatitis B surface antigen (HBsAg) and an immunostimulatory sequence (ISS) of from 8 to 50 nucleotides in length comprising an unmethylated cytosine-phosphate-guanosine (CpG) motif, wherein the subject has a glucose metabolism disorder selected from the group consisting of type I diabetes, type II diabetes, and pre-diabetes at the onset of the administering; and wherein the HBsAg and the ISS are present in the immunogenic composition in amounts effective to elicit an immune response in the subject by two months after the second dose. In some preferred embodiments, the present disclosure provides methods for eliciting a seroprotective immune response against HBV in a diabetic human subject, comprising: administering to a diabetic human subject a first and a second dose of an immunogenic composition on two separate occasions (e.g., first dose at week 0 and a second dose at week 4), wherein the immunogenic composition comprises a hepatitis B surface antigen (HBsAg) and an immunostimulatory sequence (ISS) of from 8 to 50 nucleotides in length comprising an unmethylated cytosine-phosphate-guanosine (CpG) motif, wherein the HBsAg and the ISS are present in the immunogenic composition in amounts effective to elicit a seroprotective immune response comprising an anti-HBsAg concentration of at least 10 mIU/ml in the subject by two months after the second dose. In some embodiments, the methods further comprise administering a subunit vaccine comprising HBsAg adsorbed to alum as a subsequent dose (e.g., a booster at least 6 months after the first dose, preferably at least 1 year, 5 years or 10 years after the first dose). In some embodiments, the ISS comprises the nucleotide sequence 5'-TCG-3'. In some embodiments, the ISS comprises the nucleotide sequence '5-CGTTCG-3' or '5-AACGTTCG-3'. In some embodiments, the ISS comprises the nucleotide sequence of SEQ ID NO: 1. In other embodiments, the ISS comprises the nucleotide sequence of SEQ ID NO: 2. In some preferred embodiments, the ISS comprises a phosphate backbone modification. In some preferred embodiments, the ISS comprises a phosphorothioate backbone modification. In some embodiments, the ISS is single-stranded. In some embodiments, the ISS is double-stranded. In some preferred embodiments, the ISS is 1018 ISS. In some embodiments, the immunogenic composition comprises 20 µg or less (e.g., 0.2-20 µg) of the HBsAg. In some embodiments, the immunogenic composition comprises 3000 µg or less (e.g., 30-3000 µg) of the ISS. In some preferred embodiments, the immunogenic composition comprises about 20 µg of the HBsAg and about 3000 µg of the ISS. In some embodiments, the immunogenic composition further comprises a buffer. In some embodiments, the buffer comprises sodium phosphate and sodium chloride. In some preferred embodiments, the immunogenic composition is buffered from pH 6.5 to 7.5, or to about pH 7.0. In some embodiments, the immunogenic composition further comprises a surfactant. In a subset of these embodiments, the surfactant comprises polysorbate. In some embodiments, the immunogenic composition further comprises an additional adjuvant. In a subset of these embodiments, the additional adjuvant is comprises alum. In some preferred embodiments, the HBsAg is a recombinant HBsAg produced in yeast. In some preferred embodiments, the immune response is a seroprotective antibody response comprising an anti-HBsAg response of at least 10 mIU/mL by two months after the second dose. In a subset of these embodiments, the anti-HBsAg response is at least 15, 20, or 25 mIU/mL by two months after the second dose. In some embodiments, the immune response is a seroprotective antibody response comprising an anti-HBsAg response of at least 10 mIU/mL by six months after the second dose. In a subset of these embodiments, the anti-HBsAg response is at least 20, 30, 40 or 50 mIU/mL by six months after the second dose. In some preferred embodiments, the seroprotective antibody response is statistically greater than that elicited by administration of a control immunogenic composition lacking the ISS. In some preferred embodiments, the subject has type II diabetes. In some embodiments, the subject is taking one or both of an oral hypoglycemic and insulin, at the onset of the administering. In some embodiments, the oral hypoglycemic comprises one or more of the group consisting of a biguanide, a sulfonylurea, a nonsulfonylurea secretagogue, an alpha glucosidase inhibitor, and a thiazolidinedione. In some embodiments, the biguanide is metformin. In some embodiments, the insulin is recombinant human insulin or an analog thereof. In some embodiments, the human subject is a diabetic human subject with chronic kidney disease. In some preferred embodiments, the subject has a body mass index of greater than 25 kg/m$^2$ (overweight). In other preferred embodiments, the subject has a body mass index of greater than 30 kg/m$^2$ (obese), or a body mass index of greater than 40 kg/m$^2$ (morbidly obese). In some embodiments, the subject is a resident of a nursing home or an assisted living facility. In other embodiments, the subject is a resident of a correctional facility. In some embodiments, the subject is over 40 years of age or 40 years of age or older. In a subset of these embodiments, the subject is from 41 to 60 or 61 to 80 years of age. In some preferred embodiments, the HBsAg comprises the S antigen. In other preferred embodiments, the HBsAg further comprises one or both of the pre-S2 antigen, and the pre-S1 antigen. In some embodiments, the HBsAg antigen is purified from plasma of an HBV-infected subject. In other embodiments, the HBsAg antigen is a recombinant HBsAg produced in mammalian cells in vitro. In further embodiments, the present disclosure provides methods for eliciting an immune response against hepatitis B virus (HBV) in a human subject having a glucose metabolism disorder, comprising: administering to a human subject an effective amount of an immunogenic composition, wherein the immunogenic composition comprises a hepatitis B surface antigen (HBsAg), and an immunostimulatory sequence (ISS) of from 8 to 50 nucleotides in length comprising an unmethylated cytosine-phosphate-guanosine (CpG) motif, and wherein the subject has a glucose metabolism disorder selected from the group consisting of type I diabetes, type II diabetes, and pre-diabetes at the onset of the administering. In some embodiments, the immunogenic composition is administered on two separate occasions as a first dose and a second dose, and the effective amount is sufficient to elicit an immune response in the subject after the second dose. Also provided are kits for eliciting an immune response against hepatitis B virus (HBV) in a human subject having a glucose metabolism disorder, comprising: an immunogenic composition comprising a hepatitis B surface antigen (HBsAg), and an immunostimulatory sequence (ISS) of from 8 to 50 nucleotides in length comprising an unmethylated cytosine-phosphate-guanosine (CpG) motif; and instructions for administering to a human subject an effective amount of the immunogenic composition, wherein the subject has a glucose metabolism disorder selected from the group consisting of type I diabetes, type II diabetes, and pre-diabetes.

Additionally, the present disclosure provides immunogenic compositions comprising an immunostimulatory sequence (ISS) and a hepatitis B surface antigen (HBsAg) for use in eliciting an immune response against hepatitis B virus (HBV) in a human subject when administered as a first dose and a second dose on two separate occasions (e.g., first dose at week 0 and a second dose at week 4), wherein the ISS is from 8 to 50 nucleotides in length comprising an unmethylated cytosine-phosphate-guanosine (CpG) motif, wherein the ISS and the HBsAg are present in the immunogenic composition in amounts effective to elicit an immune response in the subject by two months after the second dose, and wherein the subject has a glucose metabolism disorder selected from the group consisting of type I diabetes, type II diabetes, and pre-diabetes at the onset of the administering. Also provided by the present disclosure are immunogenic compositions comprising a immunostimulatory sequence (ISS) and a hepatitis B surface antigen (HBsAg) for use in preventing a human subject from being infected with a hepatitis B virus (HBV) when administered as a first dose and a second dose on two separate occasions, wherein the ISS is from 8 to 50 nucleotides in length comprising an unmethylated cytosine-phosphate-guanosine (CpG) motif, wherein the ISS and the HBsAg are present in the immunogenic composition in amounts effective to prevent the subject from becoming infected with HBV by two months after the second dose, and wherein the subject has a glucose metabolism disorder selected from the group consisting of type I diabetes, type II diabetes, and pre-diabetes at the onset of the administering. In some embodiments, the ISS comprises the nucleotide sequence 5'-TCG-3'. In some embodiments, the ISS comprises the nucleotide sequence '5-CGTTCG-3' or '5-AACGTTCG-3'. In some embodiments, the ISS comprises the nucleotide sequence of SEQ ID NO: 1. In other embodiments, the ISS comprises the nucleotide sequence of SEQ ID NO: 2. In some preferred embodiments, the ISS comprises a phosphate backbone modification. In some preferred embodiments, the ISS comprises a phosphorothioate backbone modification. In some embodiments, the ISS is single-stranded. In some embodiments, the ISS is double-stranded. In some preferred embodiments, the ISS is 1018 ISS. In some embodiments, the immunogenic composition comprises 20 µg or less (e.g., 0.2-20 µg) of the HBsAg. In some embodiments, the immunogenic composition comprises 3000 µg or less (e.g., 30-3000 µg) of the ISS. In some preferred embodiments, the immunogenic composition comprises about 20 µg of the HBsAg and about 3000 µg of the ISS. In some embodiments, the immunogenic composition further comprises a buffer. In some embodiments, the buffer comprises sodium phosphate and sodium chloride. In some preferred embodiments, the immunogenic composition is buffered from pH 6.5 to 7.5, or to about pH 7.0. In some embodiments, the immunogenic composition further comprises a surfactant. In a subset of these embodiments, the surfactant comprises polysorbate. In some embodiments, the immunogenic composition further comprises an additional adjuvant. In a subset of these embodiments, the additional adjuvant is comprises alum. In some preferred embodiments, the HBsAg is a recombinant HBsAg produced in yeast. In some preferred embodiments, the immune response is a seroprotective antibody response comprising an anti-HBsAg response of at least 10 mIU/mL by two months after the second dose. In a subset of these embodiments, the anti-HBsAg response is at least 15, 20, or 25 mIU/mL by two months after the second dose. In some embodiments, the immune response is a seroprotective antibody response comprising an anti-HBsAg response of at least 10 mIU/mL by six months after the second dose. In a subset of these embodiments, the anti-HBsAg response is at least 20, 30, 40 or 50 mIU/mL by six months after the second dose. In some preferred embodiments, the seroprotective antibody response is statistically greater than that elicited by administration of a control immunogenic composition lacking the ISS. In some preferred embodiments, the subject has type II diabetes. In some embodiments, the subject is taking one or both of an oral hypoglycemic and insulin, at the onset of the administering. In some embodiments, the oral hypoglycemic comprises one or more of the group consisting of a biguanide, a sulfonylurea, a nonsulfonylurea secretagogue, an alpha glucosidase inhibitor, and a thiazolidinedione. In some embodiments, the biguanide is metformin. In some embodiments, the insulin is recombinant human insulin or an analog thereof. In some embodiments, the human subject is a diabetic human subject with chronic kidney disease. In some preferred embodiments, the subject has a body mass index of greater than 25 kg/m$^2$ (overweight). In other preferred embodiments, the subject has a body mass index of greater than 30 kg/m$^2$ (obese), or a body mass index of greater than 40 kg/m$^2$ (morbidly obese). In some embodiments, the subject is a resident of a nursing home or an assisted living facility. In other embodiments, the subject is a resident of a correctional facility. In some embodiments, the subject is over 40 years of age or 40 years of age or older. In a subset of these embodiments, the subject is from 41 to 60 or 61 to 80 years of age. In some preferred embodiments, the HBsAg comprises the S antigen. In other preferred embodiments, the HBsAg further comprises one or both of the pre-S2 antigen, and the pre-S1 antigen. In some embodiments, the HBsAg antigen is purified from plasma of an HBV-infected subject. In other embodiments, the HBsAg antigen is a recombinant HBsAg produced in mammalian cells in vitro.

Moreover, the present disclosure provides immunogenic compositions comprising an immunostimulatory sequence (ISS) and a hepatitis B surface antigen (HBsAg) for use in preparing a medicament to elicit an immune response against hepatitis B virus (HBV) in a human subject when administered as a first dose and a second dose on two separate occasions (e.g., first dose at week 0 and a second dose at week 4), wherein the ISS is from 8 to 50 nucleotides in length comprising an unmethylated cytosine-phosphate-guanosine (CpG) motif, wherein the ISS and the HBsAg are present in the immunogenic composition in amounts effective to elicit an immune response in the subject by two months after the second dose, and wherein the subject has a glucose metabolism disorder selected from the group consisting of type I diabetes, type II diabetes, and pre-diabetes at the onset of the administering. Also provided by the present disclosure are immunogenic compositions comprising an immunostimulatory sequence (ISS) and a hepatitis B surface antigen (HBsAg) for use in preparing a medicament for preventing a human subject from being infected with a hepatitis B virus (HBV) when administered as a first dose and a second dose on two separate occasions, wherein the ISS is from 8 to 50 nucleotides in length comprising an unmethylated cytosine-phosphate-guanosine (CpG) motif, wherein the ISS and the HBsAg are present in the immunogenic composition in amounts effective to prevent the subject from becoming infected with HBV by two months after the second dose, and wherein the subject has a glucose metabolism disorder selected from the group consisting of type I diabetes, type II diabetes, and pre-diabetes at the onset of the administering. In some embodiments, the ISS comprises the nucleotide sequence 5'-TCG-3'. In some embodiments, the ISS comprises the nucleotide sequence '5-CGT-TCG-3' or '5-AACGTTCG-3'. In some embodiments, the ISS comprises the nucleotide sequence of SEQ ID NO: 1. In other embodiments, the ISS comprises the nucleotide sequence of SEQ ID NO: 2. In some preferred embodiments, the ISS comprises a phosphate backbone modification. In some preferred embodiments, the ISS comprises a phosphorothioate backbone modification. In some embodiments, the ISS is single-stranded. In some embodiments, the ISS is double-stranded. In some preferred embodiments, the ISS is 1018 ISS. In some embodiments, the immunogenic composition comprises 20 µg or less (e.g., 0.2-20 µg) of the HBsAg. In some embodiments, the immunogenic composition comprises 3000 µg or less (e.g., 30-3000 µg) of the ISS. In some preferred embodiments, the immunogenic composition comprises about 20 µg of the HBsAg and about 3000 µg of the ISS. In some embodiments, the immunogenic composition further comprises a buffer. In some embodiments, the buffer comprises sodium phosphate and sodium chloride. In some preferred embodiments, the immunogenic composition is buffered from pH 6.5 to 7.5, or to about pH 7.0. In some embodiments, the immunogenic composition further comprises a surfactant. In a subset of these embodiments, the surfactant comprises polysorbate. In some embodiments, the immunogenic composition further comprises an additional adjuvant. In a subset of these embodiments, the additional adjuvant is comprises alum. In some preferred embodiments, the HBsAg is a recombinant HBsAg produced in yeast. In some preferred embodiments, the immune response is a seroprotective antibody response comprising an anti-HBsAg response of at least 10 mIU/mL by two months after the second dose. In a subset of these embodiments, the anti-HBsAg response is at least 15, 20, or 25 mIU/mL by two months after the second dose. In some embodiments, the immune response is a seroprotective antibody response comprising an anti-HBsAg response of at least 10 mIU/mL by six months after the second dose. In a subset of these embodiments, the anti-HBsAg response is at least 20, 30, 40 or 50 mIU/mL by six months after the second dose. In some preferred embodiments, the seroprotective antibody response is statistically greater than that elicited by administration of a control immunogenic composition lacking the ISS. In some preferred embodiments, the subject has type II diabetes. In some embodiments, the subject is taking one or both of an oral hypoglycemic and insulin, at the onset of the administering. In some embodiments, the oral hypoglycemic comprises one or more of the group consisting of a biguanide, a sulfonylurea, a nonsulfonylurea secretagogue, an alpha glucosidase inhibitor, and a thiazolidinedione. In some embodiments, the biguanide is metformin. In some embodiments, the insulin is recombinant human insulin or an analog thereof. In some embodiments, the human subject is a diabetic human subject with chronic kidney disease. In some preferred embodiments, the subject has a body mass index of greater than 25 (overweight). In other preferred embodiments, the subject has a body mass index of greater than 30 (obese), or a body mass index of greater than 40 (morbidly obese). In some embodiments, the subject is a resident of a nursing home or an assisted living facility. In other embodiments, the subject is a resident of a correctional facility. In some embodiments, the subject is over 40 years of age. In a subset of these embodiments, the subject is from 41 to 60 or 61 to 80 years of age. In some preferred embodiments, the HBsAg comprises the S antigen. In other preferred embodiments, the HBsAg further comprises one or both of the pre-S2 antigen, and the pre-S1 antigen. In some embodiments, the HBsAg antigen is purified from plasma of an HBV-infected subject. In other embodiments, the HBsAg antigen is a recombinant HBsAg produced in mammalian cells in vitro.

The present disclosure further provides methods for eliciting a high rate of seroprotection against hepatitis B virus (HBV) in a hypo-responsive human population, comprising: administering to the hypo-responsive human population a first and a second dose of an immunogenic composition on two separate occasions, wherein the immunogenic composition comprises a hepatitis B surface antigen (HBsAg) and an immunostimulatory sequence (ISS) of from 8 to 50 nucleotides in length comprising an unmethylated cytosine-phosphate-guanosine (CpG) motif, and wherein the HBsAg and the ISS are present in the immunogenic composition in amounts effective to elicit a high rate of seroprotection against HBV in the hypo-responsive population by two months after the second dose. In some embodiments, the HBsAg and the ISS are present in the immunogenic composition in amounts effective to elicit a high rate of seroprotection against HBV in the hypo-responsive population by six months after the second dose. In some embodiments, the high rate of seroprotection comprises a seroprotection rate of least 60%, 65%, 70%, 75%, 80%, 85%, 90%, 91%, 92%, 93%, 94% or 95% of the hypo-responsive population receiving the immunogenic composition. Also provided are methods for eliciting a seroprotective immune response against hepatitis B virus (HBV) in a human subject who is a member of a hypo-responsive population, comprising: administering to the human subject a first and a second dose of an immunogenic composition on two separate occasions (e.g., first dose at week 0 and a second dose at week 4), wherein the immunogenic composition comprises a hepatitis B surface antigen (HBsAg) and an immunostimulatory sequence (ISS) of from 8 to 50 nucleotides in length comprising an unmethylated cytosine-phosphate-guanosine (CpG) motif, and wherein the HBsAg and the ISS are present in the immunogenic composition in amounts effective to elicit a seroprotective immune response against HBV in the human subject by two months after the second dose. In some embodiments, the HBsAg and the ISS are present in the immunogenic composition in amounts effective to elicit a seroprotective immune response against HBV in the human subject by six months after the second dose. In some embodiments, the seroprotective immune response comprises an anti-HBsAg concentration of at least 15, 20, 25, or 30 mUI/mL In some embodiments, the hypo-responsive population is selected from the group consisting of older adults, males, obese individuals, smokers, type I diabetics, type II diabetics, patients with chronic kidney disease, patients with chronic liver disease, patients receiving immunosuppressive therapy (transplant recipients), patients receiving chemotherapy (cancer patients), HIV-infected individuals, and HCV-infected individuals. In some embodiments, the hypo-responsive population comprises one or more of older adults, males, obese individuals, smokers, type I diabetics, type II diabetics, patients with chronic kidney disease, patients with chronic liver disease, patients receiving immunosuppressive therapy (transplant recipients), patients receiving chemotherapy (cancer patients), HIV-infected individuals, and HCV-infected individuals. Further variations of these methods are described in the preceding paragraphs.

Additionally, the present disclosure provides methods for eliciting a high level of seroprotection against hepatitis B virus (HBV) in a hypo-responsive human population according to an abbreviated vaccination schedule, comprising: administering to the hypo-responsive human population an immunogenic composition according to an abbreviated vaccination schedule, wherein the abbreviated vaccination schedule comprises administering a first, second and third dose of the immunogenic composition on three separate occasions, wherein the immunogenic composition comprises a hepatitis B surface antigen (HBsAg) and an immunostimulatory sequence (ISS) of from 8 to 50 nucleotides in length comprising an unmethylated cytosine-phosphate-guanosine (CpG) motif, wherein the HBsAg and the ISS are present in the immunogenic composition in amounts effective to elicit a high level of seroprotection against HBV in the hypo-responsive population by one month after the third dose. In some embodiments, the high level of seroprotection comprises a seroprotection rate of least 80%, 85%, 90%, 91%, 92%, 93%, 94% or 95% of the hypo-responsive population receiving the immunogenic composition. In some embodiments, the high level of seroprotection comprises an anti-HBsAg geometric mean concentration of at least 50, 100, 150, 200, 250, 300, 350, 400 or 450 mUI/mL. Also provided are methods for eliciting a seroprotective immune response against hepatitis B virus (HBV) in a human subject who is a member of a hypo-responsive population according to an abbreviated vaccination schedule, comprising: administering to the human subject an immunogenic composition according to an abbreviated vaccination schedule, wherein the abbreviated vaccination schedule comprises administering a first, second and third dose of the immunogenic composition on three separate occasions (e.g., first dose at week 0, a second dose at week 4, and a third dose at week 24), wherein the immunogenic composition comprises a hepatitis B surface antigen (HBsAg), and an immunostimulatory sequence (ISS) of from 8 to 50 nucleotides in length comprising an unmethylated cytosine-phosphate-guanosine (CpG) motif, wherein the HBsAg and the ISS are present in the immunogenic composition in amounts effective to elicit a seroprotective immune response comprising an anti-HBsAg concentration of at least 10 mUI/ml in the human subject by one month after the third dose. In some embodiments, the seroprotective immune response comprises an anti-HBsAg concentration of at least 15, 20, 25, or 30 mUI/mL by one month after the third dose. In some embodiments, the seroprotective immune response comprises an anti-HBsAg concentration of at least 40, 50, 100, 150, 200, 250, 300, 350, 400 or 450 mUI/mL. In some embodiments, the hypo-responsive population is selected from the group consisting of older adults, males, obese individuals, smokers, type I diabetics, type II diabetics, patients with chronic kidney disease, patients with chronic liver disease, patients receiving immunosuppressive therapy (transplant recipients), patients receiving chemotherapy (cancer patients), HIV-infected individuals, and HCV-infected individuals. In some embodiments, the hypo-responsive population comprises one or more of older adults, males, obese individuals, smokers, diabetics (type I diabetics and type II diabetics) and patients with chronic kidney disease. In some embodiments, the human subject has chronic kidney disease. In some embodiments, the human subject has chronic kidney disease and diabetes. In some embodiments, the ISS comprises the nucleotide sequence 5'-TCG-3'. In some embodiments, the ISS comprises the nucleotide sequence '5-CGTTCG-3' or '5-AACGTTCG-3'. In some embodiments, the ISS comprises the nucleotide sequence of SEQ ID NO: 1. In other embodiments, the ISS comprises the nucleotide sequence of SEQ ID NO: 2. In some preferred embodiments, the ISS comprises a phosphate backbone modification. In some preferred embodiments, the ISS comprises a phosphorothioate backbone modification. In some embodiments, the ISS is single-stranded. In some embodiments, the ISS is double-stranded. In some preferred embodiments, the ISS is 1018 ISS. In some embodiments, the immunogenic composition comprises 20 µg or less (e.g., 0.2-20 µg) of the HBsAg. In some embodiments, the immunogenic composition comprises 3000 µg or less (e.g., 30-3000 µg) of the ISS. In some preferred embodiments, the immunogenic composition comprises about 20 µg of the HBsAg and about 3000 µg of the ISS. In some embodiments, the immunogenic composition further comprises a buffer. In some embodiments, the buffer comprises sodium phosphate and sodium chloride. In some preferred embodiments, the immunogenic composition is buffered from pH 6.5 to 7.5, or to about pH 7.0. In some embodiments, the immunogenic composition further comprises a surfactant. In a subset of these embodiments, the surfactant comprises polysorbate. In some embodiments, the immunogenic composition further comprises an additional adjuvant. In a subset of these embodiments, the additional adjuvant is comprises alum. In some preferred embodiments, the HBsAg is a recombinant HBsAg produced in yeast. In some preferred embodiments, the HBsAg comprises the S antigen. In other preferred embodiments, the HBsAg further comprises one or both of the pre-S2 antigen, and the pre-S1 antigen. In some embodiments, the HBsAg antigen is purified from plasma of an HBV-infected subject. In other embodiments, the HBsAg antigen is a recombinant HBsAg produced in mammalian cells in vitro. Further variations of these methods are described in the preceding paragraphs.

Moreover, the present disclosure provides methods for quickly eliciting an immune response against hepatitis B virus (HBV) in a hypo-responsive human population, comprising: administering to the hypo-responsive human population a first and a second dose of an immunogenic composition on two separate occasions, wherein the immunogenic composition comprises a hepatitis B surface antigen (HBsAg) and an immunostimulatory sequence (ISS) of from 8 to 50 nucleotides in length comprising an unmethylated cytosine-phosphate-guanosine (CpG) motif, wherein the HBsAg and the ISS are present in the immunogenic composition in amounts effective to elicit an immune response comprising an anti-HBsAg geometric mean concentration of at least 5 mUI/mL in the hypo-responsive population by two months after the second dose. In some embodiments, the anti-HBsAg geometric mean concentration is at least 7.5, 10, 15 or 20 mUI/mL. Also provided are methods for quickly eliciting an immune response against hepatitis B virus (HBV) in a human subject who is a member of a hypo-responsive population, comprising: administering to the human subject a first and a second dose of an immunogenic composition on two separate occasions (e.g., first dose at week 0, and a second dose at week 4), wherein the immunogenic composition comprises a hepatitis B surface antigen (HBsAg) and an immunostimulatory sequence (ISS) of from 8 to 50 nucleotides in length comprising an unmethylated cytosine-phosphate-guanosine (CpG) motif, wherein the HBsAg and the ISS are present in the immunogenic composition in amounts effective to elicit an immune response comprising an anti-HBsAg concentration of at least 5 mUI/mL in the human subject by two months after the second dose. In some embodiments, the anti-HBsAg concentration is at least 7.5, 10, 15 or 20 mUI/mL by two months after the second dose. In some embodiments, the hypo-responsive population is selected from the group consisting of older adults, males, obese individuals, smokers, type I diabetics, type II diabetics, patients with chronic kidney disease, patients with chronic liver disease, patients receiving immunosuppressive therapy (transplant recipients), patients receiving chemotherapy (cancer patients), HIV-infected individuals, and HCV-infected individuals. In some embodiments, the hypo-responsive population comprises one or more of older adults, males, obese individuals, smokers, diabetics (type I diabetics and type II diabetics), and patients with chronic kidney disease. In some embodiments, the ISS comprises the nucleotide sequence 5'-TCG-3'. In some embodiments, the ISS comprises the nucleotide sequence '5-CGTTCG-3' or '5-AACGTTCG-3'. In some embodiments, the ISS comprises the nucleotide sequence of SEQ ID NO: 1. In other embodiments, the ISS comprises the nucleotide sequence of SEQ ID NO: 2. In some preferred embodiments, the ISS comprises a phosphate backbone modification. In some preferred embodiments, the ISS comprises a phosphorothioate backbone modification. In some embodiments, the ISS is single-stranded. In some embodiments, the ISS is double-stranded. In some preferred embodiments, the ISS is 1018 ISS. In some embodiments, the immunogenic composition comprises 20 µg or less (e.g., 0.2-20 µg) of the HBsAg. In some embodiments, the immunogenic composition comprises 3000 µg or less (e.g., 30-3000 µg) of the ISS. In some preferred embodiments, the immunogenic composition comprises about 20 µg of the HBsAg and about 3000 µg of the ISS. In some embodiments, the immunogenic composition further comprises a buffer. In some embodiments, the buffer comprises sodium phosphate and sodium chloride. In some preferred embodiments, the immunogenic composition is buffered from pH 6.5 to 7.5, or to about pH 7.0. In some embodiments, the immunogenic composition further comprises a surfactant. In a subset of these embodiments, the surfactant comprises polysorbate. In some embodiments, the immunogenic composition further comprises an additional adjuvant. In a subset of these embodiments, the additional adjuvant is comprises alum. In some preferred embodiments, the HBsAg is a recombinant HBsAg produced in yeast. In some preferred embodiments, the HBsAg comprises the S antigen. In other preferred embodiments, the HBsAg further comprises one or both of the pre-S2 antigen, and the pre-S1 antigen. In some embodiments, the HBsAg antigen is purified from plasma of an HBV-infected subject. In other embodiments, the HBsAg antigen is a recombinant HBsAg produced in mammalian cells in vitro. Further variations of these methods are described in the preceding paragraphs.

Furthermore, the present disclosure provides methods for eliciting a durable immune response against hepatitis B virus (HBV) in a hypo-responsive human population according to an abbreviated vaccination schedule, comprising: administering to the hypo-responsive human population an immunogenic composition according to an abbreviated vaccination schedule, wherein the abbreviated vaccination schedule comprises administering a first, second and third dose of the immunogenic composition on three separate occasions, wherein the immunogenic composition comprises a hepatitis B surface antigen (HBsAg) and an immunostimulatory sequence (ISS) of from 8 to 50 nucleotides in length comprising an unmethylated cytosine-phosphate-guanosine (CpG) motif, and wherein the HBsAg and the ISS are present in the immunogenic composition in amounts effective to elicit a durable immune response comprising an anti-HBsAg geometric mean concentration of at least 50, 75, 100, 150, 200 or 250 mUI/mL the hypo-responsive population 6 months or later after the third dose. Also provided are methods for eliciting a durable immune response against hepatitis B virus (HBV) in a human subject of a hypo-responsive population according to an abbreviated vaccination schedule, comprising: administering to the human subject an immunogenic composition according to an abbreviated vaccination schedule, wherein the abbreviated vaccination schedule comprises administering a first, second and third dose of the immunogenic composition on three separate occasions (e.g., first dose at week 0, a second dose at week 4, and a third dose at week 24), wherein the immunogenic composition comprises a hepatitis B surface antigen (HBsAg) and an immunostimulatory sequence (ISS) of from 8 to 50 nucleotides in length comprising an unmethylated cytosine-phosphate-guanosine (CpG) motif, and wherein the HBsAg and the ISS are present in the immunogenic composition in amounts effective to elicit a durable immune response comprising an anti-HBsAg concentration of at least 50, 75, 100, 150, 200 or 250 mUI/mL in the human subject 6 months or later after the third dose. In some embodiments, the hypo-responsive population is selected from the group consisting of older adults, males, obese individuals, smokers, type I diabetics, type II diabetics, patients with chronic kidney disease, patients with chronic liver disease, patients receiving immunosuppressive therapy (transplant recipients), patients receiving chemotherapy (cancer patients), HIV-infected individuals, and HCV-infected individuals. In some embodiments, the durable immune response comprises an anti-HBsAg concentration of at least 100 mIU/mL in the human subject at one month after the third dose. In some embodiments, the hypo-responsive population comprises one or more of older adults, males, obese individuals, smokers, diabetics (type I diabetics and type II diabetics) and patients with chronic kidney disease. In some embodiments, the human subject has chronic kidney disease. In some embodiments, the human subject has chronic kidney disease and diabetes. In some embodiments, the ISS comprises the nucleotide sequence 5'-TCG-3'. In some embodiments, the ISS comprises the nucleotide sequence '5-CGTTCG-3' or '5-AACGTTCG-3'. In some embodiments, the ISS comprises the nucleotide sequence of SEQ ID NO: 1. In other embodiments, the ISS comprises the nucleotide sequence of SEQ ID NO: 2. In some preferred embodiments, the ISS comprises a phosphate backbone modification. In some preferred embodiments, the ISS comprises a phosphorothioate backbone modification. In some embodiments, the ISS is single-stranded. In some embodiments, the ISS is double-stranded. In some preferred embodiments, the ISS is 1018 ISS. In some embodiments, the immunogenic composition comprises 20 µg or less (e.g., 0.2-20 µg) of the HBsAg. In some embodiments, the immunogenic composition comprises 3000 µg or less (e.g., 30-3000 µg) of the ISS. In some preferred embodiments, the immunogenic composition comprises about 20 µg of the HBsAg and about 3000 µg of the ISS. In some embodiments, the immunogenic composition further comprises a buffer. In some embodiments, the buffer comprises sodium phosphate and sodium chloride. In some preferred embodiments, the immunogenic composition is buffered from pH 6.5 to 7.5, or to about pH 7.0. In some embodiments, the immunogenic composition further comprises a surfactant. In a subset of these embodiments, the surfactant comprises polysorbate. In some embodiments, the immunogenic composition further comprises an additional adjuvant. In a subset of these embodiments, the additional adjuvant is comprises alum. In some preferred embodiments, the HBsAg is a recombinant HBsAg produced in yeast. In some preferred embodiments, the HBsAg comprises the S antigen. In other preferred embodiments, the HBsAg further comprises one or both of the pre-S2 antigen, and the pre-S1 antigen. In some embodiments, the HBsAg antigen is purified from plasma of an HBV-infected subject. In other embodiments, the HBsAg antigen is a recombinant HBsAg produced in mammalian cells in vitro. Further variations of these methods are described in the preceding paragraphs.

BRIEF DESCRIPTION OF DRAWINGS

FIG. 4 depicts the level of seroprotection provided by immunization of subjects with diabetes and chronic kidney disease with HEPLISAV® or ENGERIX-B® respectively.

GENERAL TECHNIQUES

Figure 1:
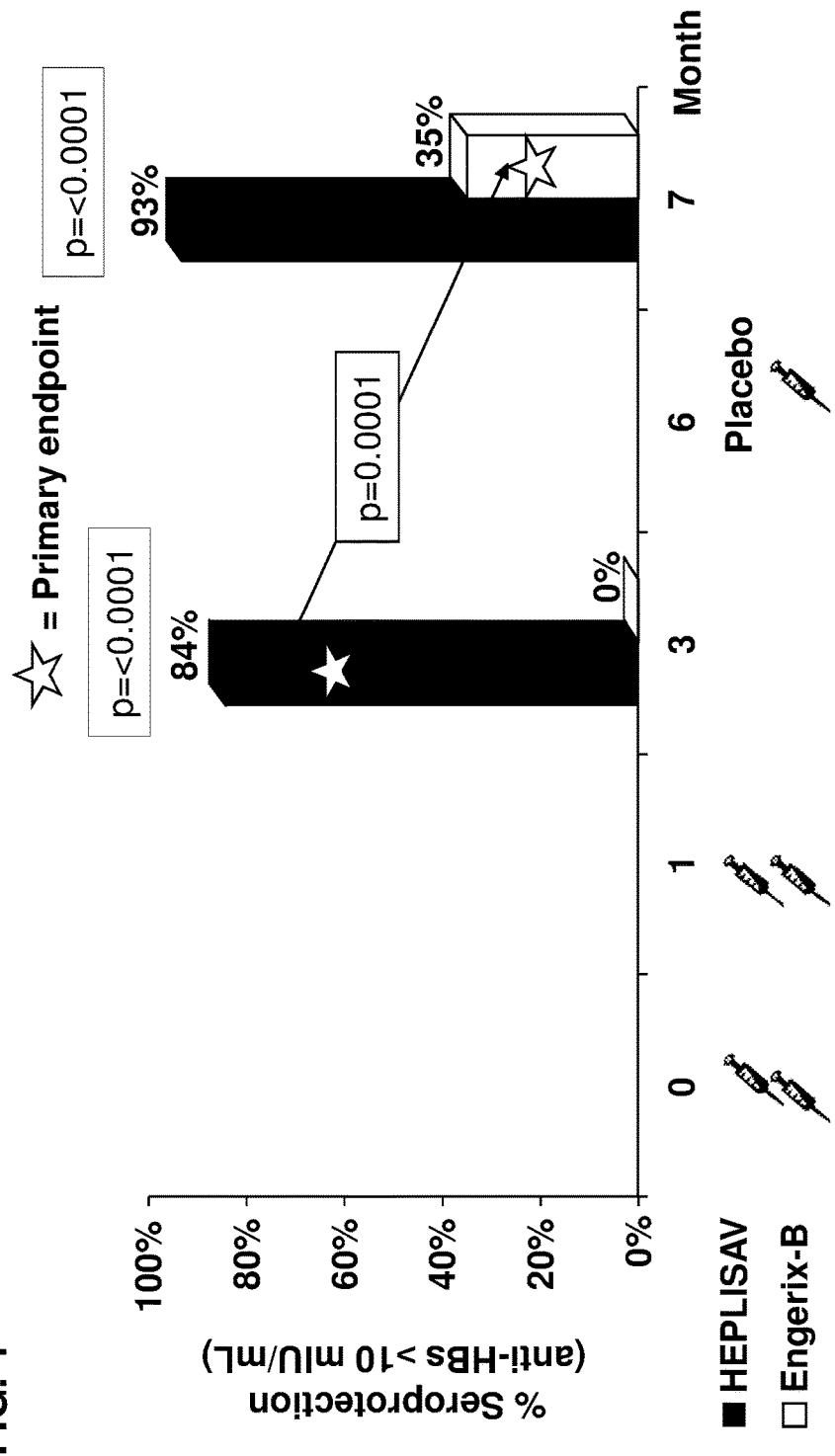
FIG. 1 depicts the level of seroprotection provided by immunization of diabetic subjects with HEPLISAV® or ENGERIX-B® respectively.

The practice of the present disclosure will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989); *Oligonucleotide Synthesis* (Gait, ed., 1984); *Animal Cell Culture* (Freshney, ed., 1987); *Handbook of Experimental Immunology* (Weir & Blackwell, eds.); *Gene Transfer Vectors for Mammalian Cells* (Miller & Calos, eds., 1987); *Current Protocols in Molecular Biology* (Ausubel et al., eds., 1987); PCR: *The Polymerase Chain Reaction*, (Mullis et al., eds., 1994); *Current Protocols in Immunology* (Coligan et al., eds., 1991); *The Immunoassay Handbook* (Wild ed., Stockton Press N.Y., 1994); *Bioconjugate Techniques*

(Hermanson, ed., Academic Press, 1996); and *Methods of Immunological Analysis* (Masseyeff, Albert, and Staines, eds., Weinheim: VCH Verlags gesellschaft mbH, 1993).

Definitions

As used herein, the singular form "a", "an", and "the" includes plural references unless indicated otherwise. For example, "an" excipient includes one or more excipients.

The phrase "comprising" as used herein is open-ended, indicating that such embodiments may include additional elements. In contrast, the phrase "consisting of" is closed, indicating that such embodiments do not include additional elements (except for trace impurities). The phrase "consisting essentially of" is partially closed, indicating that such embodiments may further comprise elements that do not materially change the basic characteristics of such embodiments.

As used interchangeably herein, the terms "polynucleotide" and "oligonucleotide" include single-stranded DNA (ssDNA), double-stranded DNA (dsDNA), single-stranded RNA (ssRNA) and double-stranded RNA (dsRNA), modified oligonucleotides and oligonucleosides or combinations thereof. The oligonucleotide can be linearly or circularly configured, or the oligonucleotide can contain both linear and circular segments. Oligonucleotides are polymers of nucleosides joined, generally, through phosphodiester linkages, although alternate linkages, such as phosphorothioate esters may also be used in oligonucleotides. A nucleoside consists of a purine (adenine (A) or guanine (G) or derivative thereof) or pyrimidine (thymine (T), cytosine (C) or uracil (U), or derivative thereof) base bonded to a sugar. The four nucleoside units (or bases) in DNA are called deoxyadenosine, deoxyguanosine, thymidine, and deoxycytidine. A nucleotide is a phosphate ester of a nucleoside.

The term "immunostimulatory sequence" or "ISS" as used herein refers to a CpG-containing oligonucleotide in which the C is unmethylated, and which contributes to a measurable immune response as measured in vitro, in vivo and/or ex vivo. Examples of measurable immune responses include, but are not limited to, antigen-specific antibody production, secretion of cytokines, activation or expansion of lymphocyte populations such as NK cells, CD4+ T lymphocytes, CD8+ T lymphocytes, B lymphocytes, and the like. Preferably, the ISS preferentially activates a Th1-type response.

An "effective amount" or a "sufficient amount" of a substance is that amount sufficient to effect beneficial or desired results, including clinical results, and, as such, an "effective amount" depends upon the context in which it is being applied. In the context of administering an immunogenic composition, an effective amount contains sufficient ISS and HBsAg to elicit an immune response (preferably a seroprotective level of antibody to HBsAg or anti-HBsAg). An effective amount can be administered in one or more doses.

The term "about" as used herein in reference to a value, encompasses from 90% to 110% of that value (e.g., about 20 µg HBsAg refers to 1.8 µg to 22 µg HBsAg).

The term "dose" as used herein in reference to an immunogenic composition refers to a measured portion of the immunogenic composition taken by (administered to or received by) a subject at any one time.

As used herein the term "immunization" refers to a process that increases an organisms' reaction to antigen and therefore improves its ability to resist or overcome infection.

The term "vaccination" as used herein refers to the introduction of vaccine into a body of an organism.

The phrase "abbreviated vaccination schedule" as used herein refers to a vaccination time table that is shorter than a standard vaccination schedule (e.g., fewer total doses taken over the same or a shorter time period). For instance, an abbreviated vaccination schedule is a two dose schedule involving administration of an immunogenic composition at month 0 and month 1, as compared to a standard three dose vaccination schedule involving administration of an immunogenic composition at month 0, month 1 and month 6. In another embodiment, an abbreviated vaccination schedule is a three dose schedule involving administration of an immunogenic composition at month 0, month 1 and month 6, as compared to a standard four dose vaccination schedule involving administration of an immunogenic composition at month 0, month 1, month 2 and month 6.

"Adjuvant" refers to a substance which, when added to a composition comprising an antigen, nonspecifically enhances or potentiates an immune response to the antigen in the recipient upon exposure.

The condition of "hyperglycemia" (high blood sugar) is a condition in which the blood glucose level is too high. Typically, hyperglycemia occurs when the fasting blood glucose level rises above 180 mg/dl. Symptoms of hyperglycemia include frequent urination, excessive thirst and, over a longer time span, weight loss.

On the other hand, "hypoglycemia" (low blood sugar) is a condition in which the blood glucose level is too low. Typically, hypoglycemia occurs when the blood glucose level falls below 70 mg/dl. Symptoms of hypoglycemia include moodiness, numbness of the extremities (especially in the hands and arms), confusion, shakiness or dizziness.

The term "impaired glucose tolerance" is used to describe a person who, when given a glucose tolerance test, has a blood glucose level that falls between normal and hyperglycemic. Such a person is at a higher risk of developing diabetes, although they are not considered to have diabetes.

The term "glucose non-responsive" as used herein describes both the complete inability of cells, or islets to respond to treatment with or administration of glucose, as well as decreased responsiveness to glucose (e.g., by cells that do not produce sufficient levels of insulin in response to glucose or that require significantly higher levels of glucose to respond at normal levels).

DETAILED DESCRIPTION

The present invention relates to immunization of hyporesponsive groups of individuals. In particular, the present invention provides methods and compositions for eliciting a potent immune response to hepatitis B virus in subjects having a glucose metabolism disorder.

HEPLISAV® (recombinant HBsAg+1018 ISS vaccine developed by Dynavax Technologies Corporation) has been shown to produce a more rapid, higher titer, and sustained seroprotective antibody response in healthy adults as compared to a currently licensed hepatitis B vaccine (Barry and Cooper, Expert Opin Biol Ther, 7:1731-1737, 2007; Halperin et al., Vaccine, 21:2461-2467, 2003; Halperin et al., Vaccine, 24:20-26, 2006; Madaan, Drugs of the Future, 34:531-535, 2009; and Sung and Chan, Curr Opin Molec Ther, 8:150-155, 2006). Other CpG-containing oligodeoxynucleotides (ODN) have been shown to improve the immunogenicity of hepatitis B virus (HBV) vaccines in preclinical and clinical studies (Cooper et al., CID, 46:1310-1314, 2008; and Payette et al., Intervirology, 49:144-151, 2006).

Although ODN-containing adjuvants appear to improve the immune response in some populations of hypo-responsive subjects (e.g., older healthy adults, and patients with end stage renal disease), during development of the present disclosure, HEPLISAV was found to remarkably improve the immune response to HBsAg in diabetic subjects, as well as other hypo-responsive populations (older adults, males, obese, smokers, and patients with chronic kidney disease). In particular, the present disclosure is based on the surprising finding that HEPLISAV induces a seroprotective anti-HBsAg response (defined as an anti-HBsAg level of ≥10 mIU/mL) in diabetic subjects after only two doses. HEPLISAV also induces a seroprotective anti-HBsAg response in adults, males, obese, smokers, and patients with chronic kidney disease after only two doses. Specifically, HEPLISAV given as two doses over one month demonstrated a superior seroprotection rate as compared to a licensed HBV vaccine given as three doses over six months. Additionally, HEPLISAV induces a seroprotective anti-HBsAg response in patients with chronic kidney disease (CKD) including CKD patients with type II diabetes after two doses, and a high titer anti-HBsAg response (100 mIU/ml or greater) after three doses. This observation is in stark contrast to published recommendations for administration of four double doses containing twice the concentration of HBsAg to hypo-responsive populations.

Hypo-Responsive Subjects

Microbial infections cause an increase in morbidity and mortality in several patient populations. For instance, influenza virus infection is more likely to cause serious disease in the elderly, patients having pre-existing cardiovascular, renal, diabetic or pulmonary disease, and immunocompromised individuals (Dorrell et al., International Journal of STD & AIDS, 8:776-770, 1997). Individuals with diabetes mellitus have a higher incidence of infection than non-diabetic individuals. The increase in susceptibility to infection by diabetics is in large part a consequence of defects in their immune response (Geerlings and Hoepelman, FEMS Immunol Med Microbial, 26:259-265, 1999). Importantly, diabetics in assisted care facilities are at increased risk of HBV infection (Tohme et al., Vaccine, 29:9316-9320, 2011), which highlights the need for an effective vaccine for these individuals.

Diabetic subjects have been reported to mount a suboptimal immune response following hepatitis B vaccination (Pozzilli et al., Diabetologia, 30:817-819, 1987; and Alavian and Tabatabaei, Vaccine, 28:3773-3777, 2010). For this reason, supplementary hepatitis B vaccinations are recommended for diabetic patients (Douvin et al., Diabetes Care, 20:148-151, 1997; and Wismans et al., J Med Virol, 35:216-222, 1991). Similarly, double doses of an HBV vaccine and/or a further booster are indicated for patients with renal disease (Beran, Expert Opin Biol Ther, 8:235-247, 2008; and Alavian and Tabatabaei, supra, 2010).

The present disclosure provides methods and compositions for inducing a seroprotective immune response to hepatitis B virus surface antigen in hyporesponsive subjects. In some embodiments, the hypo-responsive subject is an individual with a glucose metabolism disorder. In some embodiments, the glucose metabolism disorder is type I diabetes, type II diabetes, or pre-diabetes. In some embodiments, the hypo-responsive subject is a member of one or more of the groups consisting of older adults (40 years of age or older), males, obese individuals (body mass index of 30 kg/m² or greater), smokers, patients with chronic kidney disease (glomerular filtration rate of 45 mL/min/1.73 m² or less) and diabetics. In some embodiments, the hypo-responsive subject is HIV+ and/or HCV+. In some embodiments, the hypo-responsive individual has chronic liver disease. In some embodiments, the hypo-responsive subject is receiving immunosuppressive therapy or chemotherapy at the onset of the administration of the immunogenic composition. In some embodiments, the hypo-responsive subject is a member of multiple hypo-responsive groups.

As used herein in connection with groups of individuals, the term "hypo-responsive" refers to groups of people that are known to mount substantially inferior immune responses to a subunit vaccine in comparison to a normal group of study subjects. An exemplary normal group of study subjects are healthy young adults (e.g., under the age of 40). As used herein in reference to a group of individuals, the term "population" refers to at least 10, 25, 50, 100, 250, 500, 1,000 or more individuals who share a given characteristic (e.g., smokers). As used herein, the term "population" refers to a plurality of individuals, but does not require that the individuals live in the same locale. Additionally in reference to the methods of the present disclosure, the phrase "administering to a population" does not require that the population receive the immunogenic composition at the same locale or at the same time. That is the individuals of the defined population simply receive the defined immunogenic composition according to the defined immunization schedule.

Diabetes mellitus is a heterogeneous group of metabolic diseases that lead to chronic elevation of glucose in the blood (hyperglycemia). Diabetes is characterized by pancreatic islet destruction or dysfunction leading to loss of glucose regulation. The two major types of diabetes mellitus are type I diabetes, also known as insulin-dependent diabetes (IDDM) or juvenile-onset diabetes, and type II diabetes, also known as non-insulin dependent (NIDDM) or adult-onset diabetes. Subjects with a plasma glucose level of greater than or equal to 11.1 mmol/L (200 mg/dL) two hours after a 75 g oral glucose load as in a glucose tolerance test are considered to be diabetic.

Type I diabetes results from an autoimmune-mediated destruction of pancreatic beta-cells. This results in a loss of insulin production and hyperglycemia. Type I diabetics require insulin replacement therapy to regulate their blood glucose levels.

Type II diabetes, in contrast, is characterized by hyperglycemia in the presence of higher-than-normal levels of plasma insulin (hyperinsulinemia). Type II diabetes represents over 90% of all cases, and occurs most often in overweight adults over 40 years of age. Progression of type II diabetes is associated with an increase in blood glucose, coupled with a relative decrease in the rate of glucose-induced insulin secretion. In type II diabetes, physiological processes that control carbohydrate metabolism are thought to have decreased sensitivity to insulin. Thus, treatment of type II diabetes frequently does not require administration of insulin, but may instead be based on diet and lifestyle changes, augmented by therapy with oral hypoglycemic agents.

Pre-diabetes is a condition in which blood glucose levels are higher than normal, yet below that for a diagnosis of diabetes. This condition is sometimes called impaired fasting glucose (IFG) or impaired glucose tolerance (IGT), depending on the test used to diagnose it. People with pre-diabetes are at increased risk of developing type II diabetes, formerly called adult-onset diabetes or noninsulin-dependent diabetes. Subjects with fasting glucose levels from 100 to 125 mg/dL (5.6 to 6.9 mmol/L) are considered to have impaired fasting glucose, while subjects with plasma glucose at or above 140 mg/dL (7.8 mmol/L), but not over 200 mg/dL (11.1 mmol/L), two hours after a 75 g oral glucose load are considered to have impaired glucose tolerance.

Injectable insulin replacement therapy utilizes one or more of rapid-acting, short-acting, intermediate-acting and long-acting insulin formulations (WebMD website termed "Types of Insulin for Diabetes Treatment". Rapid-acting insulin formulations include but are not limited to Humalog, Lispro, Novolog, Aspart, Apidra and Glulisine. Short-acting insulin formulations include but are not limited to Humulin, Novolin and Velosulin. Intermediate-acting insulin formulations include but are not limited to NPH (N) and Lente (L). Long-acting insulin formulations include but are not limited to Ultralente (U), Lantus, Levemir and Detemir.

Oral hypoglycemic agents for treatment of type II diabetes include but are not limited to biguanides, sulfonylureas, meglitinides, thiazolidinediones, and alpha-glucosidase inhibitors (Agency for Healthcare Research and Quality website termed "Oral Diabetes Medications Fact Sheet". Metformin is a biquanide marketed as Glucophage. Sulfonylureas include but are not limited to tobutamide, acetohemamide, tolazamide, chlorpropamide, glimepiride, glipizide, glyburide and gliclazide. Meglitinides include but are not limited to repaglinide and nateglinide. Thiazolidinediones include but are not limited to pioglitazone and rosiglitazone. Alpha-glucosidase inhibitors include but are not limited to acarbose and miglitol.

Immunostimulatory Sequences (ISS)

Bacterial DNA possesses immunostimulatory properties absent in vertebrate DNA. These properties are related to the higher frequency of unmethylated cytosine-phosphate-guanosine (CpG) motifs and to the absence of cytosine methylation in bacterial DNA (Bird, Nature, 321:209-213, 1986: and Pisetsky, Immunity, 5:303-310, 1996). The effects of bacterial DNA can be mimicked using synthetic oligonucleotides. Optimal immunostimulatory sequences (ISS) often contain palindromic hexamers following the general formula of: 5'-purine-purine-CG-pyrimidine-pyrimidine-3', (Tokunaga et al., Microbiol Immunol, 36:55-66, 1992; and Yamamoto et al., J Immunol, 148:4072-4076, 1992). ISS activity is also noted with certain non-palindromic CpG-enriched phosphorothioate oligonucleotides. ISS activity may be affected by changes in the nucleotide sequence. For instance, ISS activity is abolished by cytosine methylation of the C within the CpG dinucleotide.

Bacterial DNA and synthetic oligonucleotides containing ISS have multiple effects on the immune system. These include induction of B-cell proliferation and immunoglobulin production, secretion of interferon (IFN)-α, IFN-β, interleukin (IL)-12, and IL-18 by macrophages and IFN-γ secretion from natural killer cells (Krieg et al., Nature, 374:546-549, 1995; Klinman et al., Proc Natl Acad Sci USA, 93:2879-2883, 1996; and Messina et al., J Immunol, 147:1759-1764, 1991; Sato et al., Science, 273:352-354, 1996; Yamamoto et al., Japn J Cancer Res, 79:866-873, 1988; Halpern et al., Cell Immunol, 167:72-78, 1996; Roman et al., Nat Med, 3:849-854, 1997; and Cowdery et al., J Immunol, 156:4570-4575, 1996). Therefore, ISS appears to stimulate the innate immune system to produce IFN-γ and inducers of IFN-γ (IFN-α, IFN-β, IL-12 and IL-18) and foster a cytokine milieu that greatly facilitates the induction of T cells that provide help for antibody production, especially those of the T-helper1 (Th1) phenotype.

Researchers at Dynavax (Berkeley, Calif.) have identified a 22-mer phosphorothioate 2'-deoxyribonucleotide, 1018 ISS, that contains a specific sequence that can substantially enhance the immune response to co-administered antigens. 1018 ISS was chosen after screening a broad panel of oligonucleotides for immunostimulatory activity in vitro and in vivo. 1018 ISS (5'-TGACTGTGAA CGTTCGAGAT GA-3', set forth as SEQ ID NO: 1) is active in mice, rabbits, dogs, baboons, cynomolgus monkeys and in vitro in human cells. Co-administration of 1018 ISS with protein antigens profoundly influences the magnitude and quality of the immune response to the antigens, including an increase in the overall antibody response to antigens. Consistent with this Th1-type response, 1018 ISS also significantly increases cytotoxic T lymphocyte (CTL) responses to protein antigens (Cho et al., Nat Biotechnol, 18:509-514, 2000; and Tighe et al., Eur J Immunol, 30:1939-1947, 2000).

The methods and compositions of the present disclosure comprise an ISS comprising an unmethylated cytosine-phosphate-guanosine (CpG) motif. In some preferred embodiments, the ISS comprises TCG in which the C is unmethylated, and which is from 8 to 100 nucleotides, preferably 8 to 50 nucleotides, or preferably 8 to 25 nucleotides in length. In some embodiments, the ISS comprises TCG in which the C is unmethylated, and which is from 8 to 200 nucleotides (bases or base pairs) in length. In some embodiments, the ISS is at least 8, 10, 15, or 20 nucleotides in length and is less than 50, 75, 100, 125, 150, 175 or 200 nucleotides in length. In some embodiments, the ISS is a 1018 ISS or a 1018 ISS-like oligonucleotide. The 1018 ISS consists of 22 nucleotides. The 1018-like ISS comprises 5'-AACGTTCG-3'. In some embodiments, the 1018-like ISS is at least 10, 15, or 20 nucleotides in length. In some preferred embodiments, the 1018 ISS-like oligonucleotide is less than 100 nucleotides in length, preferably less than 50, 40 or 30 nucleotides in length. For the sake of brevity, the CpG-containing ISS, the TCG-containing ISS, the 1018 ISS and the 1018 ISS-like oligonucleotides of the present disclosure are referred to below simply as an "ISS of the present disclosure" or "ISS." In some embodiments, the ISS is single-stranded, while in other embodiments, it is double-stranded. In some preferred embodiments, the ISS comprises a phosphate backbone modification. In some preferred embodiments, the ISS comprises a phosphorothioate backbone modification. In some embodiments, the ISS comprises 5'-TCGTCGTTTT GTCGTTTTGT-CGTT-3' (SEQ ID NO: 2).

Specifically, an ISS of the present disclosure may contain modifications. Modifications include any known in the art, but are not limited to, modifications of the 3'OH or 5'OH group, modifications of the nucleotide base, modifications of the sugar component, and modifications of the phosphate group. Modified bases may be included in the palindromic sequence of the ISS as long as the modified base(s) maintains the same specificity for its natural complement through Watson-Crick base pairing (e.g., the palindromic portion is still self-complementary). The ISS may be linear, circular or include circular portions and/or a hairpin loop. The ISS may be single stranded or double stranded. The ISS may be DNA or RNA.

The ISS may contain naturally-occurring or modified, non-naturally occurring bases, and may contain modified sugar, phosphate, and/or termini. For example, in addition to phosphodiester linkages, phosphate modifications include, but are not limited to, methyl phosphonate, phosphorothioate, phosphoramidate (bridging or non-bridging), phosphotriester and phosphorodithioate and may be used in any combination. Other non-phosphate linkages may also be used. In some embodiments, polynucleotides comprise only phosphorothioate backbones. In some embodiments, polynucleotides comprise only phosphodiester backbones. In some embodiments, an ISS may comprise a combination of phosphate linkages in the phosphate backbone such as a combination of phosphodiester and phosphorothioate linkages.

An ISS of the present disclosure can be synthesized using techniques and nucleic acid synthesis equipment, which are well known in the art including, but not limited to, enzymatic methods, chemical methods, and the degradation of larger oligonucleotide sequences. Naturally-occurring DNA or RNA, containing phosphodiester linkages, is generally synthesized by sequentially coupling the appropriate nucleoside phosphoramidite to the 5'-hydroxy group of the growing oligonucleotide attached to a solid support at the 3'-end, followed by oxidation of the intermediate phosphite triester to a phosphate triester. Once the desired polynucleotide sequence has been synthesized, the polynucleotide is removed from the support, the phosphate triester groups are deprotected to phosphate diesters and the nucleoside bases are deprotected using aqueous ammonia or other bases (see, e.g., Beaucage, "Oligodeoxyribonucleotide Synthesis" in Protocols for Oligonucleotides and Analogs, Synthesis and Properties (Agrawal, ed.) Humana Press, Totowa, N.J., 1993).

The ISS can also contain phosphate-modified polynucleotides, some of which are known to stabilize the polynucleotide. Accordingly, some embodiments include stabilized immunomodulatory polynucleotides. Synthesis of polynucleotides containing modified phosphate linkages or non-phosphate linkages is also known in the art (see, e.g., Matteucci "Oligonucleotide Analogs: an Overview" in Oligonucleotides as Therapeutic Agents, (Chadwick and Cardew, ed. John Wiley and Sons, New York, N.Y., 1997). The phosphorous derivative (or modified phosphate group), which can be attached to the sugar or sugar analog moiety in the polynucleotides of the present disclosure can be a monophosphate, diphosphate, triphosphate, alkylphosphonate, phosphorothioate, phosphorodithioate, phosphoramidate or the like. The preparation of the above-noted phosphate analogs, and their incorporation into nucleotides, modified nucleotides and oligonucleotides is known in the art, and therefore not described here in detail (Peyrottes et al., *Nucleic Acids Res.* 24:1841-1848, 1996; Chaturvedi et al., *Nucleic Acids Res.* 24:2318-2323, 1996; and Schultz et al., *Nucleic Acids Res.* 24:2966-2973, 1996). For example, synthesis of phosphorothioate oligonucleotides is similar to that described above for naturally occurring oligonucleotides except that the oxidation step is replaced by a sulfurization step (Zon "Oligonucleoside Phosphorothioates" in Protocols for Oligonucleotides and Analogs, Synthesis and Properties (Agrawal, ed.) Humana Press, pp. 165-190, 1993). Similarly the synthesis of other phosphate analogs, such as phosphotriester (Miller et al., *JAGS* 93:6657-6665, 1971), non-bridging phosphoramidates (Jager et al., *Biochem.* 27:7247-7246, 1988), N3' to P5' phosphoramidates (Nelson et al., TOC 62:7278-7287, 1997) and phosphorodithioates (U.S. Pat. No. 5,453,496) has also been described. Other non-phosphorous based modified oligonucleotides can also be used (Stirchak et al., Nucleic Acids Res. 17:6129-6141, 1989). Polynucleotides with phosphorothioate backbones can be more immunogenic than those with phosphodiester backbones and appear to be more resistant to degradation after injection into the host (Braun et al., *J. Immunol.* 141:2084-2089, 1988; and Latimer et al., *Mol. Immunol.* 32:1057-1064, 1995).

Hepatitis B Surface Antigen (HBsAg)

Methods for preparing HBsAg are well documented (see, Valenzuela et al., Nature 298:347-350, 1982; U.S. Pat. Nos. 4,710,463, 6,268,122, 6,270,955, and 6,297,355 to Murray; U.S. Pat. Nos. 4,769,238, 6,475,489, and 6,544,757 to Rutter et al.). As used herein, the expression "hepatitis B surface antigen" or "HBsAg" includes any HBsAg antigen or fragment thereof displaying the antigenicity of the HBV surface antigen. In addition to the 226 amino acid sequence of the HBsAg S antigen (Tiollais et al., Nature, 317:489, 1985), HBsAg may, if desired, contain all or part of a pre-S sequence. HBsAg as used herein may also refer to mutants, for example the "escape mutant" wherein HBsAg comprises a substitution of glycine to arginine at position 145. In preferred embodiments, the HBsAg is in particle form. In preferred embodiments, the HBsAg is a particle produced recombinantly in yeast. In other embodiments, the HBsAg is produced recombinantly in mammalian cells. In other embodiments, the HBsAg is purified from the plasma of an infected subject.

Four serotypes or subtypes of the hepatitis B surface antigen (HBsAg) have been defined by common determinant (a) and two mutually exclusive determinant pairs (d/y and w/r). These subtypes are adw, ayw, adr and ayr (Magnius and Norder, Intervirology, 38:24-34, 1995). The immunogenic compositions of the present disclosure are suitable for immunizing a hypo-responsive subject against infection caused by all subtypes of HBV.

Immunogenic Compositions and Administration Thereof

The immunogenic compositions for use with the methods disclosed herein, comprise 1018 ISS or a 1018 ISS-like oligonucleotide and a hepatitis B virus surface antigen. The immunogenic compositions may further comprise an additional adjuvant and/or a pharmaceutically acceptable excipient. Pharmaceutically acceptable excipients, including buffers, are well known in the art (see, e.g., Remington: The Science and Practice of Pharmacy, 20th edition, Mack Publishing, 2000).

Upon administration, compositions comprising an antigen, 1018 ISS or a 1018 ISS-like oligonucleotide, and optionally an additional adjuvant lead to a potentiation of an immune response to the antigen. Adjuvants are known in the art and include, but are not limited to, oil-in-water emulsions, water-in oil emulsions, alum (aluminum salts), liposomes and microparticles, including but not limited to, polystyrene, starch, polyphosphazene and polylactide/polyglycosides. Other suitable adjuvants also include, but are not limited to, MF59, DETOX™ (Ribi), squalene mixtures (SAF-1), muramyl peptide, saponin derivatives, mycobacterium cell wall preparations, monophosphoryl lipid A, mycolic acid derivatives, nonionic block copolymer surfactants, Quil A, cholera toxin B subunit, polyphosphazene and derivatives, and immunostimulating complexes (Takahashi et al., *Nature* 344:873-875, 1990), as well as others described herein. For veterinary use and for production of antibodies in non-human animals, mitogenic components of Freund's adjuvant (both complete and incomplete) can be used.

As with all immunogenic compositions, the immunologically effective amounts and method of administration of the particular formulation can vary based on the individual, what condition is to be treated and other factors evident to one skilled in the art. One factor to be considered includes the antigenicity of antigen, whether or not the ISS is administered in a mixture with, non-covalently associated with or covalently attached to the antigen. Other factors to be considered are the route of administration, number of doses to be administered, and time period between doses. A suitable dosage range is one that provides the desired modulation of immune response (e.g., stimulation of a seroprotective anti-HBsAg response).

In some embodiments, the immunogenic composition comprises from 1 μg to 50 μg HBsAg, preferably 4 to 40 μg HBsAg. In some preferred embodiments, the immunogenic composition comprises from 5 μg to 25 μg HBsAg (e.g., 5, 10, 15, 20 or 25 μg HBsAg), or more preferably from 10 μg to 20 μg HBsAg (e.g., 10, 15, or 20 μg HBsAg). In an exemplary embodiment, the immunogenic composition comprises 20 μg HBsAg. In some embodiments, the immunogenic composition comprises from 100 μg to 5000 μg of 1018 ISS or 1018 ISS-like oligonucleotide. In some preferred embodiments, the immunogenic composition comprises from 300 μg to 3000 μg, or more preferably from 500 μg to 5000 μg ISS (e.g., 500, 1000, 1500, 2000, 2500, 3000, 3500, 4000, 4500 or 5000 μg ISS), or more preferably 1000 μg to 3000 μg ISS (e.g., 1000, 1500, 2000, 2500, 3000 μg ISS). In some preferred embodiments, the immunogenic composition comprises about 20 μg HBsAg and about 3000 μg ISS.

Routes of administration include but are not limited to topical, dermal, transdermal, transmucosal, epidermal, subcutaneous, parenteral, gastrointestinal, and naso-pharyngeal and pulmonary, including transbronchial and transalveolar. In a preferred embodiment, the immunogenic composition is administered by intradermal injection. In a preferred embodiment, the immunogenic composition is administered by intramuscular injection.

In some embodiments, the immunogenic compositions of the present disclosure comprise HBsAg and a further antigen. In some preferred embodiments, the further antigen is an inactivated hepatitis A virus. In additional embodiments, the further antigen comprises one or more of the group consisting of an inactivated hepatitis A virus, a diphtheria toxoid, a tetanus toxoid, acellular pertussis, *Haemophilus influenzae* Type B (HiB), an inactivated polio virus, and an influenza virus (FLU) Particular combination vaccines within the scope of the present disclosure include: Diphtheria-Tetanus-Pertussis-Hepatitis B (DTP-HB), Diphtheria-Tetanus-Hepatitis B (DT-HB), and Diphtheria-Tetanus-Pertussis-Haemophilus-Hepatitis B (DTP-HiB-HB). Additional combinations include: Influenza-Hepatitis B (FLU-HB), and Hepatitis A-Hepatitis B (HA-HB) Other combination vaccines of the present disclosure include Human Papilloma Virus (HPV) antigen-Hepatitis B (HPV-HB), and Varicella Zoster Virus (VZV)-Hepatitis B (VZV-HB).

In some embodiments, the present disclosure provides kits that comprising an immunogenic composition and a set of instructions relating to the use of the immunogenic composition for the methods describe herein. The kits may comprise an immunogenic composition packaged appropriately. For example, if the immunogenic composition is freeze-dried power, a vial with a resilient stopper is normally used so that the powder may be easily resuspended by injecting fluid through the resilient stopper. In some embodiments, the kits comprise a device for administration (e.g., syringe and needle). The instructions relating to the use of the immunogenic composition generally include information as to dosage, schedule and route of administration for the intended methods of use.

EXAMPLES

Abbreviations: GMC (geometric mean concentration); HBcAb or anti-HBc (hepatitis B core antibody); HBcAg (hepatitis B core antigen); antibody to HBsAg, anti-HBsAg, or anti-HBs (hepatitis B surface antibody); HBsAg (hepatitis B surface antigen); HBV (hepatitis B virus); HEPLISAV (recombinant HBsAg+1018 ISS vaccine of Dynavax); ISS (immunostimulatory sequence); ITT (intent-to-treat population); mITT (modified intent to treat population); mIU/mL (milli international units/milliliter); PP (per-protocol); and SPR (seroprotective immune response, defined as [anti-HBsAg] of ≥10 mIU/mL).

Example 1

Immunogenicity of Two Doses of HEPLISAV Compared to Three Doses of an Approved Recombinant HBsAg Vaccine This example provides a description of a multicenter, phase three clinical study conducted among healthy adults, which compared the immunogenicity of two doses of HEPLISAV (HBsAg+1018 ISS vaccine of Dynavax, Berkeley, Calif.) administered over 4 weeks to three doses of ENGERIX-B (HBsAg adsorbed to alum vaccine of GlaxoSmithKline, Research Triangle Park, N.C.) administered over 24 weeks. An ad-hoc analysis was conducted to compare the immunogenicity of these two vaccine regimens among persons with type II diabetes. Diabetes was assessed by the review of recorded subject medical history and prior/concomitant use of oral hypoglycemics and/or insulin. Additionally an ad-hoc analysis was conducted to compare the immunogenicity of these two vaccine regimens among further hypo-responsive populations.

Primary Immunogenicity Objective: To compare the proportion of subjects who exhibit seroprotective immune response (SPR=anti-HBsAg antibody level ([anti-HBsAg]) ≥10 mIU/mL) when measured at Week 12 following vaccination with HEPLISAV at months 0 and 1 to the proportion of subjects who exhibit SPRs when measured at Week 28 following vaccination with ENGERIX-B at months 0, 1 and 6.

Secondary Immunogenicity Objective(s): To compare the proportion of subjects exhibiting an SPR for HEPLISAV versus ENGERIX-B when measured at Week 4.

Exploratory Immunogenicity Objective(s): To compare the proportion of subjects exhibiting an SPR for HEPLISAV versus ENGERIX-B when measured at Weeks 8, 12, 24 and 28. To describe the anti-HBsAg serum geometric mean concentrations (GMCs) observed for HEPLISAV and ENGERIX-B when calculated at Weeks 4, 8, 12, 24 and 28 (durability of response). To compare the proportion of subjects who exhibit seroprotective immune response (SPR=[anti-HBsAg]≥10 mIU/mL) when measured at Week 8 following vaccination with HEPLISAV at Weeks 0 and 4 to the proportion of subjects who exhibit SPR when measured at Week 28 following vaccination with ENGERIX-B at Weeks 0, 4, and 24.

Study Design—Diabetic Subjects. This study was conducted as a subject- and observer-blinded, randomized, controlled study of adult subjects (ages 11 to 55 years) randomized 3:1 to receive injections with either HEPLISAV (3000 μg 1018 ISS+20 μg rHBsAg) or ENGERIX-B (20 μg rHBsAg in alum). Subjects were stratified by age (11 to 39 years of age versus 40 to 55 years of age) prior to randomization.

Study Design—Other Hypo-responsive Subjects. This study was conducted as a subject- and observer-blinded, randomized, controlled study of adult subjects (ages 40 to 70 years) randomized 3:1 to receive injections with either HEPLISAV (3000 μg 1018 ISS+20 μg rHBsAg) or ENGERIX-B (20 μg rHBsAg in alum). Subjects were stratified gender, body mass index (BMI≥30 kg/m² as obese versus BMI<30 kg/m² as non-obese), and nicotine use (smokers versus non-smokers) prior to randomization.

Diabetic and other hypo-responsive subjects received a total of three intramuscular injections (active vaccine or matching placebo), given on study Day 0, Week 4 (1 month), and Week 24 (6 month). Subjects randomized to ENGERIX-B received three injections of ENGERIX-B (20 μg rHBsAg adsorbed to alum) at Weeks 0, 4 and 24. Subjects randomized to HEPLISAV received an injection of 3000 μg 1018 ISS+20 μg rHBsAg at Weeks 0 and 4, and a saline placebo at Week 24. All subjects were asked to return approximately 4 weeks after each injection to have blood drawn to measure anti-HBsAg levels and to undergo safety evaluations.

Study Population. Subjects were selected from among HBV seronegative male and female volunteers. Inclusion and exclusion criteria met by study participants included but were not limited to the listing provided below. Inclusion Criteria: serum negative for HBsAg, anti-HBsAg and anti-HBcAg. Exclusion Criteria: history of HBV infection; prior immunization with any HBV vaccine; clinically debilitating illness, (e.g., fever ≥38° C. within 72 hours prior to study injection, bleeding disorders, cancer, autoimmune disease, immunodeficiency, etc.); history or laboratory evidence of autoimmune disease; high risk for recent exposure to HBV or HIV; recent receipt of blood products or likely to require infusion of blood products; previously received DNA plasmids or oligonucleotides by injection; and recent use of systemic corticosteroids, other immunomodulators or other immunosuppressive medications (with the exception of inhaled steroids); and history of sensitivity to any component of the study vaccines.

Subjects included in the diabetes cohort were selected based on a medical history including preferred terms with DIABET, and excluding GESTATIONAL DIABETES. Additional subjects in the diabetes cohort were selected based on the use of concomitant medication (ATC code A10) for diabetes, in the absence of a documented medical history of diabetes.

Treatments Administered. HEPLISAV (3000 μg 1018 ISS+20 μg rHBsAg) was manufactured by Rentschler Biotechnologie GmbH, Laupheim, Germany for Dynavax. Technologies Corporation, Berkeley, Calif.) The rHBsAg of this formulation was derived from yeast cells transformed with an expression vector containing HBsAg (S) sequence, subtype adw. 1018 ISS is a single-stranded, 22-base phosphorothioate 2'-deoxyribo-oligonucleotide prepared by standard solid-phase chemistry techniques (5'-TGACTGTGAA CGTTCGAGAT GA-3', set forth as SEQ ID NO: 1). 1018 ISS has a molecular mass of approximately 7150 Daltons. HEPLISAV also contains the following excipients: 8 mM sodium phosphate, 154 mM sodium chloride, and 0.01% w/w polysorbate 80, pH 7.0 buffer. The HEPLISAV drug product is formulated as 6000 mcg/mL 1018 ISS and 40 mcg/mL HBsAg in a 2-mL vial containing 0.7 mL of solution (28 mcg of protein and 4200 mcg of 1018 ISS per vial) of which a 0.5 mL dose (20 mcg of protein and 3000 mcg of 1018 ISS) is administered. HEPLISAV is stored at 2 to 8° C. before use.

Immunogenicity Analyses. Two patient populations were considered for the immunogenicity analysis: the per-protocol (PP) population and the intent-to-treat (ITT) population. The immunogenicity analysis using the PP population was considered primary. PP Population-Immunogenicity: The PP population included subjects who met the eligibility criteria, did not violate the protocol in a substantial manner, received all protocol-specified study vaccinations, had their primary serology and all vaccinations within the specified day ranges, and had serology at their primary endpoint (week 12 for HEPLISAV and week 28 for ENGERIX-B). ITT Population-Immunogenicity: The ITT population included subjects who had at least one vaccination and one post baseline anti-HBsAg level. Anti-HBsAg was measured by using the hepatitis B enhanced chemiluminescence immunoassay (Hep B ECi, Ortho Clinical Diagnostics, Rochester, N.Y.).

All statistical tests comparing demographic, patient characteristic and safety data were two-sided and conducted at the 5% significance level. All immunogenicity analyses utilized one-sided tests at the 2.5% level of significance. All data analyses were performed using Statistical Analysis Systems (SAS) for Windows 95/NT (version 8.2 or later, SAS Institute, Cary, N.C.). The 95% confidence interval (CI) of SPR was calculated using the Clopper Pearson method. The 95% confidence interval (CI) of the difference (HEPLISAV−ENGRIX-B) was calculated using Newcombe score method with continuity correction. For the immunogenicity objectives, if the lower bound of 95% CI was greater than −10% then HEPLISAV was scored as non-inferior. Additionally, if HEPLISAV was scored as non-inferior, and the lower bound of the 95% CI was greater than 0%, then HEPLISAV was also scored as superior.

Seroprotective Immune Response (SPR) Rate. For the purpose of this analysis, a seroprotective immune response was defined as an anti-HBsAg concentration of ≥10 mIU/mL.

Geometric Mean Concentrations (GMCs). Anti-HBsAg GMC was measured four weeks after each active injection for both groups. All anti-HBsAg concentrations that were reported as <5.0 mIU/mL were considered as 2.5 mIU/mL in the computation for GMC. Log (base 10)-transformed anti-HBsAg concentrations were used to summarize the GMCs for the two treatment groups.

Results—Diabetic Subjects. Of the 2101 non-diabetic and diabetic subjects in the overall per protocol study population (1566 HEPLISAV, and 535 ENGERIX-B), the SPR was 95% at Week 12 in the HEPLISAV group and 81% at Week 28 in the ENGERIX-B group ($p<0.001$), indicating non-inferiority/superiority of HEPLISAV. Among the 62 diabetics in the per protocol population, 45 were in the HEPLISAV group (mean age of 44.4 years) and 17 in the ENGERIX-B group (mean age of 45.5 years). Of these subjects, 38 (84%) in the HEPLISAV group achieved SPR compared to 0 (0%) in the ENGERIX-B group at Week 12 ($p<0.0001$), and 42 (93%) versus 6 (35%) respectively at Week 28 ($p<0.0001$).

TABLE 1-1

Seroprotection (SPR) Rates of HBsAg Vaccinated Study Populations

| Week/Population | HEPLISAV # Subjects | HEPLISAV SPR Rate | ENGERIX-B # Subjects | ENGERIX-B SPR Rate | P-Value |
|---|---|---|---|---|---|
| Week 12 | | | | | |
| PP non-diabetic | 1,521 | 95.4% | 518 | 23.2% | <0.0001 |
| PP diabetic | 45 | 84.4% | 17 | 0.0% | <0.0001 |
| ITT diabetic | 54 | 85.2% | 18 | 0.0% | <0.0001 |
| Week 28 | | | | | |
| PP non-diabetic | 1,520 | 98.1% | 518 | 82.6% | <0.0001 |
| PP diabetic | 45 | 93.3% | 17 | 35.3% | <0.0001 |
| ITT diabetic | 54 | 92.6% | 18 | 33.3% | <0.0001 |

TABLE 1-2

Seroprotection (SPR) Rates in Vaccinated Per Protocol Diabetic Subjects

| Week/Population | HEPLISAV # Subjects | HEPLISAV SPR Rate | ENGERIX-B # Subjects | ENGERIX-B SPR Rate | P-Value* |
|---|---|---|---|---|---|
| Week 4 | | | | | |
| PP diabetic | 45 | 24.4% | 17 | 0% | ND |
| Week 8 | | | | | |
| PP diabetic | 45 | 71.1% | 17 | 5.9% | ND |
| Week 12 | | | | | |
| PP diabetic | 45 | 84.4% | 17 | 0% | <0.0001 |
| Week 24 | | | | | |
| PP diabetic | 45 | 93.3% | 17 | 11.8% | ND |
| Week 28 | | | | | |
| PP diabetic | 45 | 93.3% | 17 | 35.3% | <0.0001 |

*ND = Not Done.

TABLE 1-3

Anti-HBsAg Geometric Mean Concentrations (GMC) in Vaccinated Per Protocol Diabetic Subjects+

| Week/Population | HEPLISAV # Subjects | HEPLISAV GMC | ENGERIX-B # Subjects | ENGERIX-B GMC | P-Value* |
|---|---|---|---|---|---|
| Week 4 | | | | | |
| PP diabetic | 45 | 4.8 (3.5, 6.6) | 17 | 2.5 (2.5, 2.5) | ND |
| Week 8 | | | | | |
| PP diabetic | 45 | 36.7 (21.3, 63.1) | 17 | 3.2 (2.2, 4.6) | ND |
| Week 12 | | | | | |
| PP diabetic | 45 | 47.1 (29.4, 75.3) | 17 | 2.8 (2.4, 3.5) | <0.0001 |
| Week 24 | | | | | |
| PP diabetic | 45 | 109.8 (68.2, 176.7) | 17 | 3.2 (2.2, 4.7) | ND |
| Week 28 | | | | | |
| PP diabetic | 45 | 96.9 (59.4, 158.3) | 17 | 16.7 (3.8, 74.0) | 0.0283 |

+GMC (95% confidence interval).
*ND = Not done.

As determined during development of the present disclosure, in a subset analysis of adults with diabetes, HEPLISAV given as two doses over one month demonstrated superior SPR compared to ENGERIX-B given as three doses over six months. Thus, use of HEPLISAV to vaccinate diabetics provides superior protection against hepatitis B infection and disease as compared to a Food and Drug Administration approved recombinant HBV vaccine.

Figure 2:
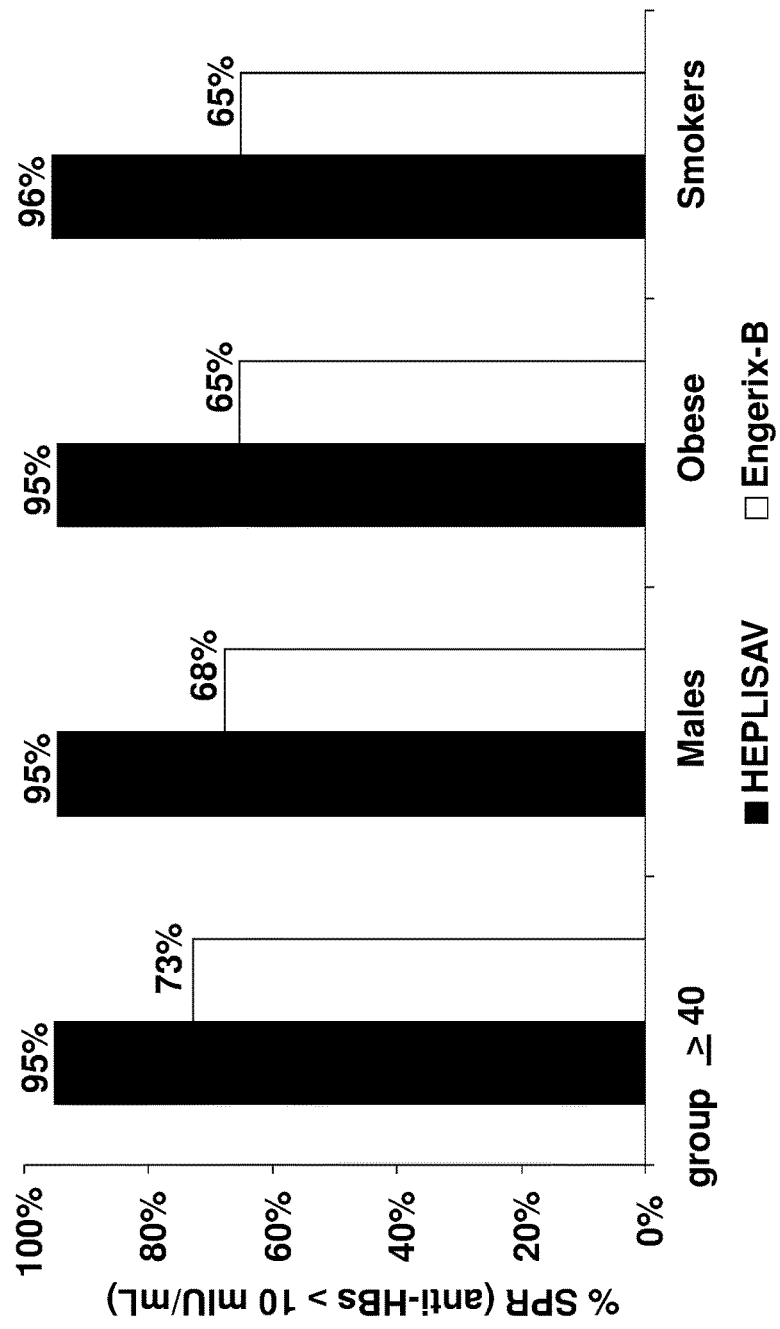
FIG. 2 depicts the peak level of seroprotection provided by immunization of various hypo-responsive populations with two doses of HEPLISAV® or three doses of ENGERIX-B® respectively.
Figure 3:
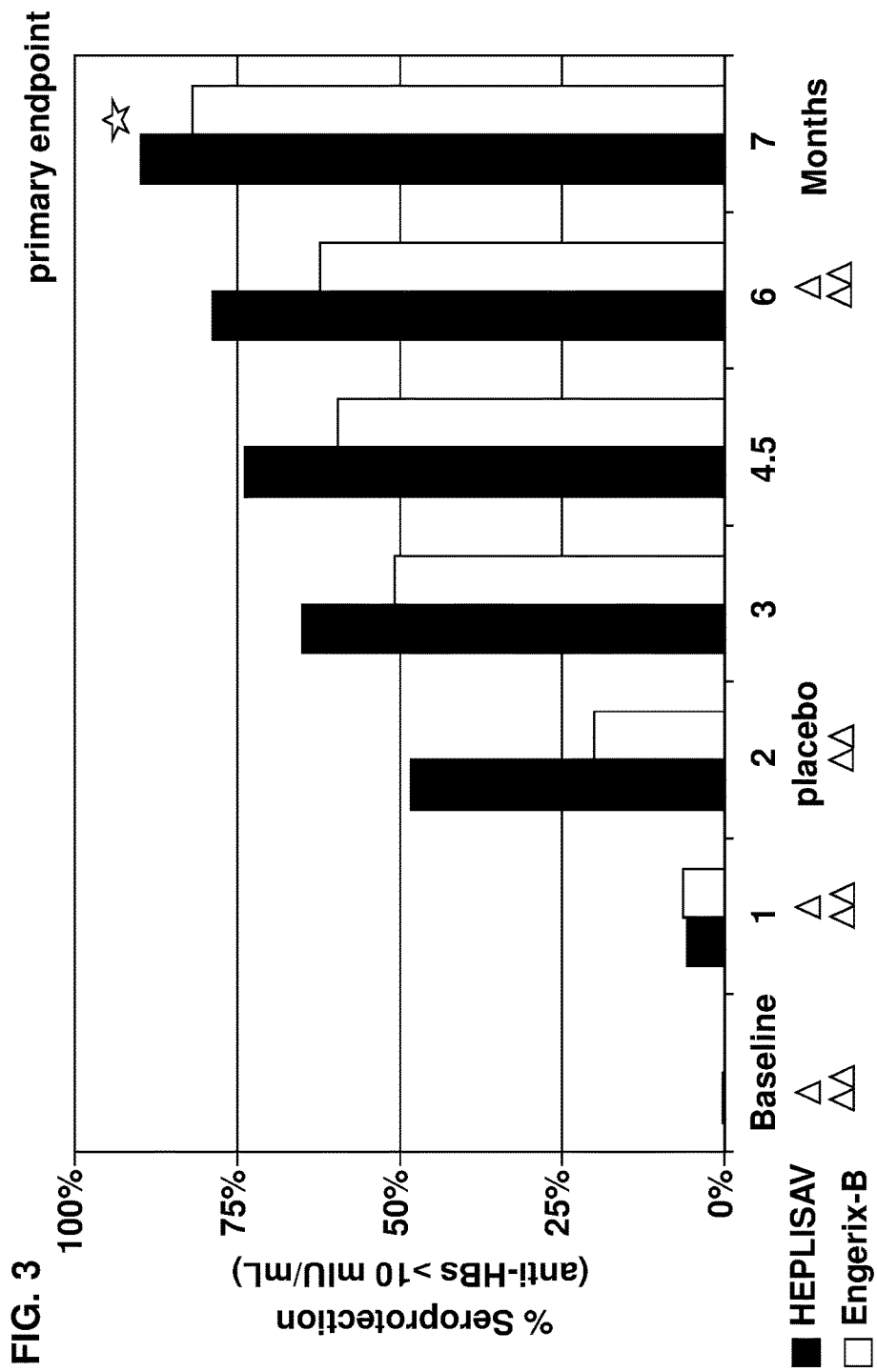
FIG. 3 depicts the level of seroprotection provided by immunization of subjects with chronic kidney disease with HEPLISAV® or ENGERIX-B® respectively.

Results—Other Hypo-responsive Subjects. Of the 1482 subjects in the overall per protocol study population (1123 HEPLISAV and 359 ENGERIX-B), the peak SPR was 95% in the HEPLISAV group at week 12 and 73% in the ENGERIX-B group at week 32 with an SPR difference of 22.3% (P<0.0001), indicating non-inferiority and superiority of HEPLISAV. Moreover, the peak SPR of HEPLISAV was superior to ENGERIX-B in all hypo-responsive subgroups (Table 1-4 and FIG. 2). Within the HEPLISAV group, the SPR was similar between males and females, obese and non-obese, and smokers and non-smokers. In the ENERIX-B group, the males, obese, and smokers were hypo-responsive in comparison to the females, non-obese, and non-smokers.

TABLE 1-4

Peak % SPR in Per Protocol Populations

| Subjects | HEPLISAV % SPR (N) | ENGERIX B % SPR (N) |
| --- | --- | --- |
| Adults ≥40 yrs | 95.1 (1123)[c] | 72.8 (359) |
| Males | 94.6 (537)[c] | 67.8 (177) |
| Females | 95.6 (586)[c] | 77.8 (180) |
| Obese[a] | 94.7 (494)[c] | 65.4 (153) |
| Non-obese[b] | 95.4 (629)[c] | 78.4 (204) |
| Smokers | 95.6 (229)[c] | 65.3 (75) |
| Non-smokers | 95.0 (894)[c] | 74.8 (282) |

[a]BMI ≥30 kg/m$^2$;
[b]BMI <30 kg/m$^2$; and
[c]P < 0.0001.

As determined during development of the present disclosure, HEPLISAV given as 2 doses over 4 weeks was superior and protected a significantly greater proportion of subjects than ENGERIX-B given as 3 doses over 24 weeks in adults overall and in groups known to be hypo-responsive to currently licensed hepatitis B vaccine. A hepatitis B vaccine that provides a greater level of seroprotection in hypo-responsive groups is an important public health advancement because it provides protection from HBV to a greater proportion of subjects.

Example 2

Immunogenicity of Three Doses of HEPLISAV Compared to Four Double Doses of an Approved Recombinant HBsAg Vaccine This example provides a description of a phase three clinical study conducted among adults with chronic kidney disease (CKD), which compared three doses of HEPLISAV (HBsAg+1018 ISS vaccine of Dynavax, Berkeley, Calif.) administered over six months to four double doses of ENGERIX-B (HBsAg adsorbed to alum vaccine of GlaxoSmithKline, Research Triangle Park, N.C.) administered over six months. CKD was defined by a GFR of less than or equal to 45 mL/min/1.73 m$^2$.

Primary Immunogenicity Objective: To compare the proportion of subjects who exhibit seroprotective immune response (SPR=anti-HBsAg antibody level ([anti-HBsAg]) ≥10 mIU/mL) when measured at Week 28 following vaccination with HEPLISAV at months 0, 1 and 6 to the proportion of subjects who exhibit SPRs when measured at Week 28 following vaccination with ENGERIX-B at months 0, 1, 2 and 6.

Other Immunogenicity Objective(s): To compare the proportion of subjects exhibiting an SPR for HEPLISAV versus ENGERIX-B at multiple time points. To describe the anti-HBsAg serum geometric mean concentrations (GMCs) observed for HEPLISAV and ENGERIX-B calculated at multiple time points (speed and durability of response).

Study Design. This study was conducted as a subject- and observer-blinded, randomized, controlled study of adult subjects (ages 18 to 75 years) with chronic kidney disease (progressive loss of renal function as defined by GFR≤45 mL/min/1.73 m$^2$) randomized to receive injections with either HEPLISAV (3000 µg 1018 ISS+20 µg rHBsAg) or ENGERIX-B (2×20 µg rHBsAg in alum). Randomization was stratified by GFR (≤15, 16-30, and 31-45 mL/min/1.73 m$^2$). All subjects received a total of four intramuscular injections (active vaccine or matching placebo), given on study Day 0 (0 month), Week 4 (1 month), Week 8 (2 month) and Week 24 (6 month). Subjects randomized to ENGERIX-B received four double-doses of ENGERIX-B (2×20 µg rHBsAg adsorbed to alum) at Weeks 0, 4, 8 and 24. Subjects randomized to HEPLISAV received three doses of HEPLISAV (3000 µg 1018 ISS+20 µg rHBsAg) at Weeks 0, 4 and 24, and a saline placebo at Week 8. All subjects were asked to return approximately 4 weeks after each injection to have blood drawn to measure anti-HBsAg levels and to undergo safety evaluations.

Study Population. Subjects were selected from among HBV seronegative male and female volunteers. Inclusion and exclusion criteria met by study participants included but were not limited to the listing provided below. Inclusion Criteria: adults with chronic kidney disease, and serum negative for HBsAg, anti-HBsAg and anti-HBcAg. Exclusion Criteria: history of HBV infection; prior immunization with any HBV vaccine; clinically debilitating illness, (e.g., fever≥38° C. within 72 hours prior to study injection, bleeding disorders, cancer, autoimmune disease, immunodeficiency, etc.); high risk for recent exposure to HBV, HCV or HIV; recent receipt of blood products or likely to require infusion of blood products; previously received DNA plasmids or oligonucleotides by injection; and recent use of systemic corticosteroids, other immunomodulators or other immunosuppressive medications (with the exception of inhaled steroids); and history of sensitivity to any component of the study vaccines.

Treatments Administered. HEPLISAV (3000 µg 1018 ISS+20 µg rHBsAg) was manufactured by Rentschler Biotechnologie GmbH, Laupheim, Germany for Dynavax Technologies Corporation, Berkeley, Calif.) The rHBsAg of this formulation was derived from yeast cells transformed with an expression vector containing HBsAg (S) sequence, subtype adw. 1018 ISS is a single-stranded, 22-base phosphorothioate 2'-deoxyribo-oligonucleotide prepared by standard solid-phase chemistry techniques (5'-TGACTGTGAA CGTTCGAGAT GA-3', set forth as SEQ ID NO: 1). 1018 ISS has a molecular mass of approximately 7150 Daltons. HEPLISAV also contains the following excipients: 8 mM sodium phosphate, 154 mM sodium chloride, and 0.01% w/w polysorbate 80, pH 7.0 buffer. The HEPLISAV drug product is formulated as 6000 mcg/mL 1018 ISS and 40 mcg/mL HBsAg in a 2-mL vial containing 0.7 mL of solution (28 mcg of protein and 4200 mcg of 1018 ISS per vial) of which a 0.5 mL dose (20 mcg of protein and 3000 mcg of 1018 ISS) is administered. HEPLISAV is stored at 2 to 8° C. before use.

Immunogenicity Analyses. Two patient populations were considered for the immunogenicity analysis: the per-protocol (PP) population and the modified intent-to-treat (mITT) population. Anti-HBsAg was measured by using the hepatitis B enhanced chemiluminescence immunoassay (Hep B ECi, Ortho Clinical Diagnostics, Rochester, N.Y.).

All statistical tests comparing demographic, patient characteristic and safety data were two-sided and conducted at the 5% significance level. All immunogenicity analyses utilized one-sided tests at the 2.5% level of significance. All data analyses were performed using Statistical Analysis Systems (SAS) for Windows 95/NT (version 8.2 or later, SAS Institute, Cary, N.C.). The 95% confidence interval (CI) of SPR was calculated using the Clopper Pearson method. The 95% confidence interval (CI) of the difference (HEPLISAV−ENGRIX-B) was calculated using Newcombe score method with continuity correction. For the immunogenicity objectives, if the lower bound of 95% CI was greater than −10% then HEPLISAV was scored as non-inferior. Additionally, if HEPLISAV was scored as non-inferior, and the lower bound of the 95% CI was greater than 0%, then HEPLISAV was also scored as superior.

Seroprotective Immune Response (SPR) Rate. For the purpose of this analysis, a seroprotective immune response was defined as an anti-HBsAg concentration of ≥10 mIU/mL.

Geometric Mean Concentrations (GMCs). Anti-HBsAg concentrations were measured at weeks 0, 4, 8, 12, 18, 24, 28, 36, 44 and 52 for both groups. All anti-HBsAg concentrations that were reported as <5.0 mIU/mL (limit of the assay) were considered as 2.5 mIU/mL in the computation for GMC. Log (base 10)-transformed anti-HBsAg concentrations were used to summarize the GMCs for the two treatment groups.

Results. The modified intent-to-treat (mITT) population included all subjects with at least one immunization and a post-immunization antibody assessment, and consisted of 507 subjects with 247 subjects in the HEPLISAV (H) group and 260 subjects in the ENGRIX-B (EB) group. 63% of H subjects and 60% of EB subjects were men. The mean age was 61 years for both groups. The mean body mass index in kg/m$^2$ was 34 for H and 32 for EB. 15% of H and 19% of EB subjects had a GFR≤15 mL/min/1.73 m$^2$. 68% of H and 61% of EB subjects were diabetic. The incidence of post-injection reactions and adverse events was similar in both groups. The SPR was 89.8% in the H group and 81.8% in the EB group, with an SPR difference of 8.0% (95% CI: 1.6%, 14.2%), indicating non-inferiority and superiority of HEPLISAV. The SPR of HEPLISAV was superior to ENGRIX-B from weeks 8 through 28. The difference in the percentage of subjects with anti-HBs ≥100 mIU/mL between H and EB was 10.6% (95% CI, 2.1%, 18.7%) at month 7. The geometric mean concentration (GMC) in H (589 mIU/mL; 95% CI, 387, 896) was significantly higher than the GMC in EB (156 mIU/mL; 95% CI, 104, 236) at month 7, with a 3.8 fold higher GMC in H. In diabetic subjects the SPR in the H group was 89.5% versus 76.7% in the EB group at month 7, with a SPR difference of 12.8% (95% CI, 4.4%, 21.2%), indicating non-inferiority and superiority of H. Further data analysis was performed to evaluate the results in CKD patients, as well as in CKD patients with and without type II diabetes, as shown in Tables 2-1 through 2-7 (weeks in bold indicate when vaccine or placebo injections were administered).

TABLE 2-1

Seroprotection Rates in mITT Subjects with Chronic Kidney Disease without Diabetes

| Week | HEPLISAV % SPR Rate | ENGERIX-B % SPR Rate | % H-E |
|---|---|---|---|
| 0 | 0 | 0 | 0 |
| 4 | 1.3 | 7.0 | −5.7 |
| 8 | 61.8 | 26.5 | 35.3 |
| 12 | 78.9 | 57.9 | 21.1 |
| 18 | 84.4 | 71.3 | 13.1 |
| 24 | 85.5 | 71.3 | 14.2 |

TABLE 2-1-continued

Seroprotection Rates in mITT Subjects with Chronic Kidney Disease without Diabetes

| Week | HEPLISAV % SPR Rate | ENGERIX-B % SPR Rate | % H-E |
|---|---|---|---|
| 28 | 90.4 | 90.2 | 0.2 |
| 36 | 91.2 | 88.2 | 3.1 |
| 44 | 87.5 | 87.0 | 0.5 |
| 52 | 85.7 | 87.5 | −1.8 |

TABLE 2-2

Seroprotection Rates in mITT Subjects with Chronic Kidney Disease with Type II Diabetes

| Week | HEPLISAV % SPR Rate | ENGERIX-B % SPR Rate | % H-E |
|---|---|---|---|
| 0 | 0.6 | 0.0 | 0.6 |
| 4 | 7.7 | 5.7 | 2.0 |
| 8 | 41.8 | 16.4 | 25.5 |
| 12 | 58.6 | 46.4 | 12.2 |
| 18 | 68.6 | 52.3 | 16.3 |
| 24 | 75.5 | 56.6 | 18.9 |
| 28 | 89.5 | 76.7 | 12.8 |
| 36 | 82.3 | 76.4 | 5.9 |
| 44 | 78.4 | 73.0 | 5.4 |
| 52 | 78.3 | 70.8 | 7.5 |

TABLE 2-3

Anti-HBsAg GMC (mIU/mL) + 95% CI in mITT Subjects with Chronic Kidney Disease

| Week | HEPLISAV GMC N = 247 | ENGERIX-B GMC N = 260 | H/E Ratio |
|---|---|---|---|
| 4 | 0.4 (0.3, 0.5) | 0.3 (0.2, 0.3) | 1.58 (1.13, 2.20) |
| 8 | 8.1 (5.6, 11.7) | 0.9 (0.7, 1.3) | 8.84 (5.45, 14.34) |
| 12 | 16.5 (11.7, 23.4) | 7.2 (5.0, 10.4) | 2.30 (1.28, 3.81) |
| 18 | 33.0 (23.4, 46.6) | 12.0 (8.4, 17.2) | 2.75 (1.67, 4.51) |
| 24 | 44.3 (31.6, 62.3) | 15.1 (10.6, 21.5) | 2.94 (1.80, 4.81) |
| 28 | 588.8 (386.9, 896) | 156.5 (103.6, 236.3) | 3.76 (2.09, 6.77) |

TABLE 2-4

Anti-HBsAg GMC (mIU/mL) + 95% CI in mITT Subjects with Chronic Kidney Disease without Diabetes

| Week | HEPLISAV GMC | ENGERIX-B GMC | H/E Ratio |
|---|---|---|---|
| 0 | 0.2 (0.2, 0.2) | 0.2 (0.2, 0.2) | 1.03 (0.91, 1.17) |
| 4 | 0.3 (0.2, 0.5) | 0.3 (0.2, 0.4) | 1.17 (0.68, 2.01) |
| 8 | 20.6 (11.6, 36.6) | 1.4 (0.8, 2.5) | =14.66 (6.53, 32.90) |
| 12 | 33.7 (19.6, 57.8) | 12.1 (6.6, 22.0) | 2.79 (1.23, 6.32) |
| 18 | 62.8 (36.1, 109.3) | 24.3 (14.0, 42.3) | 2.58 (1.18, 5.66) |
| 24 | 80.0 (45.4, 140.9) | 27.2 (15.8, 47.0) | 2.94 (1.34, 6.45) |
| 28 | 999.0 (466.3, 2140.1) | 280.8 (153.1, 515.2) | 3.56 (1.37, 9.24) |

TABLE 2-4-continued

Anti-HBsAg GMC (mIU/mL) + 95% CI in mITT Subjects with Chronic Kidney Disease without Diabetes

| Week | HEPLISAV GMC | ENGERIX-B GMC | H/E Ratio |
|---|---|---|---|
| 36 | 558.7 | 197.1 | 2.83 |
|  | (242.0, 1290.1) | (105.7, 367.5) | (1.03, 7.79) |
| 44 | 313.6 | 170.0 | 1.84 |
|  | (112.8, 871.8) | (84.9, 340.5) | (0.57, 5.98) |
| 52 | 273.1 | 113.8 | 2.40 |
|  | (98.6, 756.4) | (50.4, 256.7) | (0.67, 8.54) |

TABLE 2-5

Anti-HBsAg GMC (mIU/mL) + 95% CI in mITT Subjects with Chronic Kidney Disease with Type II Diabetes

| Week | HEPLISAV GMC | ENGERIX-B GMC | H/E Ratio |
|---|---|---|---|
| 0 | 0.2 | 0.2 | 1.03 |
|  | (0.2, 0.2) | (0.2, 0.2) | (0.93, 1.14) |
| 4 | 0.4 | 0.2 | 1.87 |
|  | (0.3, 0.6) | (0.2, 0.3) | (1.23, 2.85) |
| 8 | 5.3 | 0.7 | 7.49 |
|  | (3.4, 8.3) | (0.5, 1.0) | (4.13, 13.57) |
| 12 | 11.8 | 5.2 | 2.27 |
|  | (7.6, 18.3) | (3.3, 8.3) |  |
| 18 | 24.2 | 7.8 | 3.1 |
|  | (15.7, 37.2) | (4.9, 12.4) | (1.66, 5.81) |
| 24 | 33.4 | 10.4 | 3.20 |
|  | (22.0, 50.9) | (6.6, 16.6) | (1.72, 5.95) |
| 28 | 456.8 | 109.3 | 4.18 |
|  | (276.1, 755.7) | (63.1, 189.1) |  |
| 36 | 186.7 | 71.5 | 2.61 |
|  | (108.7, 320.6) | (39.6, 129.3) | (1.18, 5.79) |
| 44 | 111.1 | 44.0 | 2.53 |
|  | (63.7, 194.0) | (22.7, 85.2) | (1.08, 5.93) |
| 52 | 104.9 | 30.0 | 3.50 |
|  | (51.9, 212.1) | (14.0, 64.4) | (1.25, 9.76) |

TABLE 2-6

Anti-HBsAg ≥100 mIU/mL Rates in mITT Subjects with Chronic Kidney Disease without Diabetes

| Week | HEPLISAV % SPR Rate | ENGERIX-B % SPR Rate | %☐ H-E |
|---|---|---|---|
| 0 | 0 | 0 | 0 |
| 4 | 1.3 | 4.0 | -2.7 |
| 8 | 34.2 | 9.2 | 25.0 |
| 12 | 36.8 | 24.2 | 12.6 |
| 18 | 46.8 | 31.9 | 14.8 |
| 24 | 56.6 | 35.1 | 21.5 |
| 28 | 80.8 | 67.4 | 13.4 |
| 36 | 78.9 | 63.2 | 15.8 |
| 44 | 77.5 | 64.8 | 12.7 |
| 52 | 78.6 | 60.0 | 18.6 |

TABLE 2-7

Anti-HBsAg ≥100 mIU/mL Rates in mITT Subjects with Chronic Kidney Disease with Type II Diabetes

| Week | HEPLISAV % SPR Rate | ENGERIX-B % SPR Rate | %☐ H-E |
|---|---|---|---|
| 0 | 0 | 0 | 0 |
| 4 | 4.8 | 1.9 | 2.9 |
| 8 | 12.7 | 5.7 | 7.0 |
| 12 | 22.8 | 20.9 | 1.9 |
| 18 | 34.6 | 22.2 | 12.4 |
| 24 | 39.6 | 24.3 | 15.3 |
| 28 | 70.4 | 60.7 | 9.7 |
| 36 | 64.6 | 55.3 | 9.3 |
| 44 | 60.8 | 52.8 | 8.0 |
| 52 | 60.0 | 46.2 | 14.7 |

In a Phase 3 trial of adults 18-75 years of age with chronic kidney disease, three doses of the investigational vaccine HEPLISAV demonstrated both non-inferiority and superiority to eight doses of the licensed vaccine ENGERIX-B as determined by measuring seroprotection at week 28, meeting the primary immunogenicity objective. Similarly, in a subset of chronic kidney disease patients with diabetes, HEPLISAV demonstrated both non-inferiority and superiority to ENGERIX-B. The two vaccines have similar safety profiles as shown in Table 2-8.

TABLE 2-8

Adverse Experience (AE) Summary

| Subjects with | HEPLISAV N = 254 | ENGERIX-B N = 262 |
|---|---|---|
| One or more AE | 76% | 75% |
| Related AE | 8% | 9% |
| Post-injection reactions | 47% | 51% |
| systemic | 34% | 35% |
| pain | 28% | 34% |
| Severe AE | 23% | 26% |
| Death | 2.8% | 1.1% |

Tables 2-1 and 2-2 demonstrate that the seroprotection rates in mITT subjects with chronic kidney disease are significantly higher from weeks 8-24 for the subjects treated with HEPLISAV compared to ENGERIX-B. Tables 2-3 through 2-5 show that anti-HBsAg GMC in mITT subjects with chronic kidney disease are significantly higher from weeks 8-52 for the subjects treated with HEPLISAV compared to ENGERIX-B. Tables 2-6 and 2-7 demonstrate that anti-HBsAg ≥100 mIU/mL rates in mITT subjects with chronic kidney disease are significantly higher from weeks 8-52 for the subjects treated with HEPLISAV compared to ENGERIX-B. Higher antibody levels in individuals and higher GMCs in the population provide longer lasting protection indicating that fewer and less frequent HEPLISAV boosters are required to maintain seroprotection.

Given the hypo-responsiveness of patients with chronic kidney disease to licensed hepatitis B vaccines and the increased risk of infection in dialysis patients, the availability of a vaccine that provides an earlier response, is more effective using fewer doses, and is more durable in these patients promises to contribute substantially to prevention of HBV infections.

Although the foregoing disclosure has been described in some detail by way of illustration and example for purposes of clarity and understanding, it will be apparent to those skilled in the art that certain changes and modifications may be practiced. Therefore, descriptions and examples should not be construed as limiting the scope of the disclosure.

I claim:

1. A method for eliciting a seroprotective immune response against hepatitis B virus (HBV) in a human subject with chronic kidney disease under a vaccination schedule, comprising:
   administering to the human subject a first, second and third dose of an immunogenic composition comprising a hepatitis B surface antigen (HBsAg) and an immunostimulatory sequence (ISS) present in the immunogenic composition in amounts effective to elicit a seroprotective immune response comprising an anti-HBsAg concentration of at least 10 mIU/mL in the subject at one month after only three doses,
   wherein said ISS is single stranded and consists of the nucleotide sequence of SEQ ID NO:1, and wherein said immunogenic composition comprises from about 10 to about 20 μg of said HBsAg and from about 1000 to about 3000 μg of said ISS.

2. A method for eliciting a durable immune response against hepatitis B virus (HBV) in a human subject with chronic kidney disease under a vaccination schedule, comprising:
   administering to the human subject a first, second and third dose of an immunogenic composition comprising a hepatitis B surface antigen (HBsAg) and an immunostimulatory sequence (ISS) present in the immunogenic composition in amounts effective to elicit a durable immune response comprising an anti-HBsAg concentration of at least 100 mIU/mL in the subject at 28 weeks after only three doses,
   wherein said ISS is single stranded and consists of the nucleotide sequence of SEQ ID NO:1, and wherein said immunogenic composition comprises from about 10 to about 20 μg of said HBsAg and from about 1000 to about 3000 μg of said ISS.

3. The method of claim 1, wherein the seroprotective immune response comprises a durable immune response comprising an anti-HBsAg concentration of at least 100 mIU/mL in the subject at 28 weeks after only three doses.

4. The method of claim 1, wherein the subject has diabetes.

5. The method of claim 1, wherein said ISS comprises a phosphate backbone modification.

6. The method of claim 5, wherein said phosphate backbone modification comprises a phosphorothioate backbone modification.

7. The method of claim 6, wherein said immunogenic composition further comprises a buffer and a surfactant.

8. The method of claim 6, wherein said immunogenic composition comprises about 20 μg of said HBsAg and about 3000 μg of said ISS.

9. The method of claim 6, wherein said immunogenic composition comprises about 20 μg of said HBsAg.

10. The method of claim 6, wherein said immunogenic composition comprises about 3000 μg of said ISS.

11. The method of claim 1, wherein said HBsAg is a recombinant HBsAg produced in yeast.

12. The method of claim 1, wherein said subject does not have diabetes.

13. The method of claim 12, wherein said seroprotective immune response further comprises an anti-HBsAg concentration of at least 10 mIU/mL in the subject at eight weeks after only two doses.

14. The method of claim 1, wherein said vaccination schedule has a satisfactory safety profile.

* * * * *